(12) United States Patent
Zhang et al.

(10) Patent No.: US 8,023,130 B2
(45) Date of Patent: Sep. 20, 2011

(54) METHODS AND SYSTEMS FOR IMAGING DEVICE ACCOUNTING DATA MAINTENANCE

(75) Inventors: Hanzhong Zhang, Cypress, CA (US); David J. Lovat, Huntington Beach, CA (US)

(73) Assignee: Sharp Laboratories of America, Inc., Camas, WA (US)

(*) Notice: Subject to any disclaimer, the term of this patent is extended or adjusted under 35 U.S.C. 154(b) by 1255 days.

(21) Appl. No.: 11/192,865

(22) Filed: Jul. 29, 2005

(65) Prior Publication Data

US 2006/0077433 A1     Apr. 13, 2006

Related U.S. Application Data

(63) Continuation-in-part of application No. 10/962,248, filed on Oct. 8, 2004, and a continuation-in-part of application No. 10/961,793, filed on Oct. 8, 2004, and a continuation-in-part of application No. 10/961,911, filed on Oct. 8, 2004, and a continuation-in-part of application No. 10/961,594, filed on Oct. 8, 2004, and a continuation-in-part of application No. 10/962,103, filed on Oct. 8, 2004.

(60) Provisional application No. 60/704,066, filed on Jul. 28, 2005.

(51) Int. Cl.
G06F 3/12 (2006.01)
G06F 15/167 (2006.01)

(52) U.S. Cl. ......... 358/1.15; 399/10; 709/211; 709/216; 709/220; 709/223; 705/2

(58) Field of Classification Search .......... 358/1.1–1.15; 399/79, 10; 709/216, 223, 220, 211; 705/30, 705/2; 707/202, 204, 10; 714/13–14, 16; 711/162
See application file for complete search history.

(56) References Cited

U.S. PATENT DOCUMENTS

| | | | |
|---|---|---|---|
| 5,085,587 A | 2/1992 | DesForges et al. | |
| 5,228,100 A | 7/1993 | Takeda et al. | |
| 5,323,393 A | 6/1994 | Barrett et al. | |
| 5,365,494 A | 11/1994 | Lynch | |
| 5,410,646 A | 4/1995 | Tondevold et al. | |
| 5,504,589 A | 4/1996 | Montague et al. | |

(Continued)

FOREIGN PATENT DOCUMENTS

EP         1160657         12/2001

(Continued)

OTHER PUBLICATIONS

F.D. Wright, Design Goals for an Internet Printing Protocol, Apr. 1999, pp. 1-43, http://tools.ietf.org/html/rfc2567.

(Continued)

Primary Examiner — Twyler Haskins
Assistant Examiner — Dennis Dicker
(74) Attorney, Agent, or Firm — Krieger Intellectual Property, Inc.; Scott C. Krieger

(57) ABSTRACT

Aspects of the present invention relate to systems, methods and devices for maintaining imaging device (IDev) accounting data in the event that an imaging device's primary accounting server becomes unavailable. Some aspects relate to the use of a lightweight accounting backup server (LABS) that may reside on an imaging device, a networked computer or another computing device for the purpose of storing and communication accounting data when a primary accounting server fails.

12 Claims, 15 Drawing Sheets

U.S. PATENT DOCUMENTS

| | | | |
|---|---|---|---|
| 5,513,112 A * | 4/1996 | Herring et al. ................ 705/404 |
| 5,659,845 A | 8/1997 | Krist et al. |
| 5,671,412 A | 9/1997 | Christiano |
| 5,699,493 A | 12/1997 | Davidson et al. |
| 5,699,494 A | 12/1997 | Colbert et al. |
| 5,717,439 A | 2/1998 | Levine et al. |
| 5,726,883 A | 3/1998 | Levine et al. |
| 5,727,082 A | 3/1998 | Sugishima |
| 5,727,135 A | 3/1998 | Webb et al. |
| 5,745,883 A | 4/1998 | Krist et al. |
| 5,760,775 A | 6/1998 | Sklut et al. |
| 5,774,678 A | 6/1998 | Motoyama |
| 5,791,790 A | 8/1998 | Bender et al. |
| 5,796,934 A * | 8/1998 | Bhanot et al. ...................... 714/4 |
| 5,799,206 A | 8/1998 | Kitagawa et al. |
| 5,799,289 A | 8/1998 | Fukushima et al. |
| 5,812,818 A | 9/1998 | Adler et al. |
| 5,832,264 A | 11/1998 | Hart et al. |
| 5,877,776 A | 3/1999 | Beaman et al. |
| 5,944,824 A | 8/1999 | He |
| 5,956,487 A | 9/1999 | Venkatraman et al. |
| 5,956,698 A | 9/1999 | Lacheze et al. |
| 5,968,127 A | 10/1999 | Kawabe et al. |
| 5,993,088 A | 11/1999 | Nogay et al. |
| 5,995,553 A | 11/1999 | Crandall et al. |
| 5,999,708 A | 12/1999 | Kajita |
| 6,042,384 A | 3/2000 | Loiacono |
| 6,044,382 A | 3/2000 | Martino |
| 6,069,706 A | 5/2000 | Kajita |
| 6,075,860 A | 6/2000 | Ketcham |
| 6,115,132 A | 9/2000 | Nakatsuma et al. |
| 6,118,546 A | 9/2000 | Sanchez |
| 6,128,731 A | 10/2000 | Zarrin et al. |
| 6,141,662 A | 10/2000 | Jeyachandran |
| 6,148,346 A | 11/2000 | Hanson |
| 6,161,139 A | 12/2000 | Win et al. |
| 6,178,308 B1 | 1/2001 | Bobrow et al. |
| 6,199,080 B1 | 3/2001 | Nielsen |
| 6,213,652 B1 | 4/2001 | Suzuki et al. |
| 6,216,113 B1 | 4/2001 | Aikens et al. |
| 6,233,409 B1 | 5/2001 | Haines et al. |
| 6,240,456 B1 | 5/2001 | Teng et al. |
| 6,246,487 B1 | 6/2001 | Kobayashi |
| 6,292,267 B1 | 9/2001 | Mori et al. |
| 6,301,016 B1 | 10/2001 | Matsueda et al. |
| 6,307,640 B1 | 10/2001 | Motegi |
| 6,311,040 B1 | 10/2001 | Kucinski et al. |
| 6,353,878 B1 * | 3/2002 | Dunham ........................ 707/204 |
| 6,369,905 B1 | 4/2002 | Mitsuhashi et al. |
| 6,426,798 B1 | 7/2002 | Yeung |
| 6,433,883 B1 | 8/2002 | Kajita |
| 6,438,589 B1 | 8/2002 | Iwata |
| 6,476,926 B1 * | 11/2002 | Yano et al. ................... 358/1.14 |
| 6,490,601 B1 | 12/2002 | Markus et al. |
| 6,510,466 B1 | 1/2003 | Cox et al. |
| 6,516,157 B1 | 2/2003 | Maruta et al. |
| 6,526,258 B2 | 2/2003 | Bejar et al. |
| 6,567,179 B1 | 5/2003 | Sato et al. |
| 6,590,673 B2 | 7/2003 | Kadowaki |
| 6,592,275 B1 | 7/2003 | Aihara et al. |
| 6,597,469 B1 | 7/2003 | Kuroyanagi |
| 6,604,157 B1 | 8/2003 | Brusky et al. |
| 6,621,422 B2 | 9/2003 | Rubenstein |
| 6,636,929 B1 | 10/2003 | Frantz et al. |
| 6,643,650 B1 | 11/2003 | Slaughter et al. |
| 6,652,169 B2 | 11/2003 | Parry |
| 6,685,637 B1 | 2/2004 | Rom |
| 6,707,466 B1 | 3/2004 | Van Sickle et al. |
| 6,721,286 B1 | 4/2004 | Williams et al. |
| 6,735,773 B1 | 5/2004 | Trinh et al. |
| 6,749,434 B2 | 6/2004 | Stuppy |
| 6,772,945 B2 | 8/2004 | Mahoney et al. |
| 6,775,729 B1 | 8/2004 | Matsuo et al. |
| 6,826,727 B1 | 11/2004 | Mohr et al. |
| 6,836,623 B2 | 12/2004 | Imai |
| 6,836,845 B1 | 12/2004 | Lennie et al. |
| 6,850,252 B1 | 2/2005 | Hoffberg |
| 6,862,110 B2 | 3/2005 | Harrington |
| 6,873,429 B2 | 3/2005 | Matsuura |
| 6,874,010 B1 | 3/2005 | Sargent |
| 6,904,412 B1 | 6/2005 | Broadbent et al. |
| 6,915,525 B2 | 7/2005 | Ozawa |
| 6,934,706 B1 | 8/2005 | Mancuso et al. |
| 6,934,740 B1 | 8/2005 | Lawande et al. |
| 6,940,532 B1 | 9/2005 | Fukui et al. |
| 6,948,175 B1 | 9/2005 | Fong et al. |
| 6,951,303 B2 | 10/2005 | Petersen et al. |
| 6,975,820 B2 | 12/2005 | Wong |
| 6,999,987 B1 | 2/2006 | Billingsley et al. |
| 7,013,289 B2 | 3/2006 | Horn et al. |
| 7,019,753 B2 * | 3/2006 | Rappaport et al. ............ 345/582 |
| 7,079,143 B2 | 7/2006 | Gilbert |
| 7,095,513 B2 | 8/2006 | Stringham |
| 7,107,615 B2 | 9/2006 | Cossel et al. |
| 7,124,097 B2 | 10/2006 | Claremont et al. |
| 7,126,717 B2 | 10/2006 | Jeyachandran |
| 7,127,700 B2 | 10/2006 | Large |
| 7,136,909 B2 | 11/2006 | Balasuriya |
| 7,136,941 B2 | 11/2006 | Nguyen et al. |
| 7,143,364 B1 | 11/2006 | Tam |
| 7,145,673 B1 | 12/2006 | Lin |
| 7,149,697 B2 | 12/2006 | Zerza et al. |
| 7,162,103 B2 | 1/2007 | Meunier et al. |
| 7,170,618 B2 | 1/2007 | Fujitani et al. |
| 7,174,056 B2 | 2/2007 | Silverbrook et al. |
| 7,177,814 B2 | 2/2007 | Gong et al. |
| 7,181,017 B1 | 2/2007 | Nagel et al. |
| 7,181,442 B2 | 2/2007 | Yeh et al. |
| 7,185,078 B2 | 2/2007 | Pleyer et al. |
| 7,188,125 B1 * | 3/2007 | Karr ............................. 707/204 |
| 7,188,181 B1 | 3/2007 | Squier et al. |
| 7,191,391 B2 | 3/2007 | Takashima |
| 7,197,615 B2 * | 3/2007 | Arakawa et al. .............. 711/162 |
| 7,203,699 B2 | 4/2007 | Bellamy |
| 7,212,301 B2 | 5/2007 | Treibach-Heck et al. |
| 7,216,347 B1 | 5/2007 | Harrison et al. |
| 7,233,929 B1 | 6/2007 | Lingle et al. |
| 7,239,409 B2 | 7/2007 | Parry |
| RE39,808 E | 9/2007 | Motegi |
| 7,272,269 B2 | 9/2007 | Tojo et al. |
| 7,275,044 B2 | 9/2007 | Chauvin et al. |
| 7,284,061 B2 | 10/2007 | Matsubayashi et al. |
| 7,293,034 B2 | 11/2007 | Paya et al. |
| 7,296,221 B1 | 11/2007 | Treibach-Heck et al. |
| 7,301,658 B2 | 11/2007 | Henry |
| 7,305,616 B1 | 12/2007 | Nelson et al. |
| 7,321,440 B2 | 1/2008 | Kimura |
| 7,325,196 B1 | 1/2008 | Covington et al. |
| 7,327,478 B2 | 2/2008 | Matsuda |
| 7,328,245 B1 | 2/2008 | Hull et al. |
| 7,343,551 B1 | 3/2008 | Bourdev |
| 7,349,949 B1 | 3/2008 | Connor et al. |
| 7,363,586 B1 | 4/2008 | Briggs et al. |
| 7,404,204 B2 | 7/2008 | Davenport et al. |
| 7,406,660 B1 | 7/2008 | Sikchi et al. |
| 7,444,519 B2 | 10/2008 | Laferriere et al. |
| 7,451,392 B1 | 11/2008 | Chalecki et al. |
| 7,454,623 B2 | 11/2008 | Hardt |
| 7,467,211 B1 | 12/2008 | Herman et al. |
| 7,496,837 B1 | 2/2009 | Larcheveque et al. |
| 7,500,178 B1 | 3/2009 | O'Donnell |
| 7,508,535 B2 | 3/2009 | Hart et al. |
| 7,509,649 B2 | 3/2009 | Shenfield |
| 7,545,528 B2 | 6/2009 | Takabayashi et al. |
| 7,548,334 B2 | 6/2009 | Lo et al. |
| 7,552,265 B2 | 6/2009 | Newman et al. |
| 7,565,554 B2 | 7/2009 | Joosten et al. |
| 7,567,360 B2 | 7/2009 | Takahashi et al. |
| 7,573,593 B2 | 8/2009 | Hart et al. |
| 7,729,363 B2 | 6/2010 | Shenfield et al. |
| 2001/0021945 A1 | 9/2001 | Matsuura |
| 2001/0027527 A1 | 10/2001 | Khidekel et al. |
| 2001/0028808 A1 | 10/2001 | Nomura et al. |
| 2001/0038462 A1 | 11/2001 | Teeuwen et al. |
| 2001/0039614 A1 | 11/2001 | Hellberg et al. |
| 2001/0044787 A1 | 11/2001 | Shwartz et al. |
| 2002/0005984 A1 | 1/2002 | Donath et al. |

| | | |
|---|---|---|
| 2002/0016921 A1 | 2/2002 | Olsen et al. |
| 2002/0029256 A1 | 3/2002 | Zintel et al. |
| 2002/0032745 A1 | 3/2002 | Honda |
| 2002/0049786 A1 | 4/2002 | Bibliowicz et al. |
| 2002/0052916 A1 | 5/2002 | Kloba et al. |
| 2002/0059265 A1 | 5/2002 | Valorose, III |
| 2002/0073148 A1 | 6/2002 | Haines et al. |
| 2002/0080381 A1 | 6/2002 | Haines |
| 2002/0089691 A1 | 7/2002 | Fertlitsch et al. |
| 2002/0093676 A1 | 7/2002 | Parry |
| 2002/0098027 A1 | 7/2002 | Koike et al. |
| 2002/0099796 A1 | 7/2002 | Chou |
| 2002/0103827 A1 | 8/2002 | Sesek |
| 2002/0105664 A1 | 8/2002 | Inoue et al. |
| 2002/0107939 A1 | 8/2002 | Ford et al. |
| 2002/0109718 A1 | 8/2002 | Mansour et al. |
| 2002/0112037 A1 | 8/2002 | Koss |
| 2002/0120792 A1 | 8/2002 | Blair |
| 2002/0138279 A1 | 9/2002 | Al-Kazily et al. |
| 2002/0138476 A1 | 9/2002 | Suwa et al. |
| 2002/0138666 A1 | 9/2002 | Fujisawa |
| 2002/0145627 A1 | 10/2002 | Whitmarsh |
| 2002/0147858 A1 | 10/2002 | Motoyama et al. |
| 2002/0152183 A1 | 10/2002 | Soares et al. |
| 2002/0152235 A1 | 10/2002 | Motoyama et al. |
| 2002/0152302 A1 | 10/2002 | Motoyama et al. |
| 2002/0156846 A1 | 10/2002 | Rawat et al. |
| 2002/0171857 A1 | 11/2002 | Hisatomi |
| 2002/0194350 A1* | 12/2002 | Lu et al. ................. 709/229 |
| 2003/0002074 A1 | 1/2003 | Miyano |
| 2003/0007170 A1 | 1/2003 | Kajita et al. |
| 2003/0011633 A1 | 1/2003 | Conley et al. |
| 2003/0011640 A1 | 1/2003 | Green et al. |
| 2003/0014515 A1 | 1/2003 | Motoyama et al. |
| 2003/0014529 A1 | 1/2003 | Simpson et al. |
| 2003/0033369 A1 | 2/2003 | Bernhard |
| 2003/0035133 A1 | 2/2003 | Berkema et al. |
| 2003/0038965 A1 | 2/2003 | Simpson et al. |
| 2003/0043205 A1 | 3/2003 | Hill |
| 2003/0043396 A1 | 3/2003 | Klosterman et al. |
| 2003/0048470 A1 | 3/2003 | Garcia |
| 2003/0048473 A1 | 3/2003 | Rosen |
| 2003/0049037 A1 | 3/2003 | Sadowara et al. |
| 2003/0053123 A1 | 3/2003 | Wu et al. |
| 2003/0063313 A1 | 4/2003 | Ito |
| 2003/0065766 A1 | 4/2003 | Parry |
| 2003/0065791 A1 | 4/2003 | Garg et al. |
| 2003/0074312 A1 | 4/2003 | White |
| 2003/0081240 A1 | 5/2003 | Soto et al. |
| 2003/0084114 A1 | 5/2003 | Simpson et al. |
| 2003/0084302 A1 | 5/2003 | de Jong et al. |
| 2003/0088642 A1 | 5/2003 | Price et al. |
| 2003/0123112 A1 | 7/2003 | Kajita et al. |
| 2003/0142351 A1 | 7/2003 | Sakura |
| 2003/0164987 A1 | 9/2003 | Enomoto et al. |
| 2003/0182632 A1 | 9/2003 | Murdock et al. |
| 2003/0184552 A1 | 10/2003 | Chadha |
| 2003/0184590 A1 | 10/2003 | Will |
| 2003/0184782 A1 | 10/2003 | Perkins |
| 2003/0187922 A1 | 10/2003 | Ohara et al. |
| 2003/0188193 A1 | 10/2003 | Venkataramappa |
| 2003/0197883 A1 | 10/2003 | Lay et al. |
| 2003/0225796 A1 | 12/2003 | Matsubara |
| 2003/0225829 A1 | 12/2003 | Pena et al. |
| 2003/0225894 A1 | 12/2003 | Ito |
| 2003/0231196 A1 | 12/2003 | Keohane et al. |
| 2004/0003341 A1 | 1/2004 | alSafadi et al. |
| 2004/0008363 A1 | 1/2004 | Suzuki et al. |
| 2004/0012628 A1 | 1/2004 | Kropf et al. |
| 2004/0012644 A1 | 1/2004 | Allen et al. |
| 2004/0030693 A1 | 2/2004 | Toda |
| 2004/0034786 A1 | 2/2004 | Okamoto et al. |
| 2004/0039990 A1 | 2/2004 | Bakar et al. |
| 2004/0044779 A1 | 3/2004 | Lambert |
| 2004/0054573 A1 | 3/2004 | Shah et al. |
| 2004/0061729 A1 | 4/2004 | Green |
| 2004/0064759 A1 | 4/2004 | McGuire et al. |
| 2004/0068693 A1 | 4/2004 | Rawat et al. |
| 2004/0070606 A1 | 4/2004 | Yang et al. |
| 2004/0080511 A1 | 4/2004 | Gilbert |
| 2004/0080771 A1 | 4/2004 | Mihira et al. |
| 2004/0080778 A1 | 4/2004 | Ito et al. |
| 2004/0093515 A1 | 5/2004 | Reeves, Jr. |
| 2004/0098165 A1 | 5/2004 | Butikofer |
| 2004/0098316 A1 | 5/2004 | Philippe et al. |
| 2004/0098595 A1 | 5/2004 | Apperle et al. |
| 2004/0105104 A1 | 6/2004 | Ishikawa et al. |
| 2004/0105122 A1 | 6/2004 | Schaeffer |
| 2004/0109028 A1 | 6/2004 | Stern et al. |
| 2004/0111670 A1 | 6/2004 | Sasakuma et al. |
| 2004/0113941 A1 | 6/2004 | Sliwa et al. |
| 2004/0117358 A1 | 6/2004 | von Kaenel et al. |
| 2004/0117784 A1 | 6/2004 | Endoh |
| 2004/0125403 A1 | 7/2004 | Furst et al. |
| 2004/0128349 A1 | 7/2004 | Maruyama |
| 2004/0130744 A1 | 7/2004 | Wu et al. |
| 2004/0130749 A1 | 7/2004 | Aoki |
| 2004/0133525 A1 | 7/2004 | Singh et al. |
| 2004/0150663 A1 | 8/2004 | Kim |
| 2004/0158471 A1 | 8/2004 | Davis et al. |
| 2004/0161257 A1 | 8/2004 | Ishihara |
| 2004/0162076 A1 | 8/2004 | Chowdry et al. |
| 2004/0165209 A1 | 8/2004 | Aoki et al. |
| 2004/0169881 A1 | 9/2004 | Sato |
| 2004/0179229 A1 | 9/2004 | Laughlin |
| 2004/0187018 A1 | 9/2004 | Owen et al. |
| 2004/0199538 A1 | 10/2004 | Matsuda et al. |
| 2004/0203358 A1 | 10/2004 | Anderson |
| 2004/0205118 A1 | 10/2004 | Yu |
| 2004/0205533 A1 | 10/2004 | Lopata et al. |
| 2004/0205620 A1 | 10/2004 | Nishikiori et al. |
| 2004/0212823 A1 | 10/2004 | Chavers et al. |
| 2004/0215671 A1 | 10/2004 | Hyakutake et al. |
| 2004/0221231 A1 | 11/2004 | Madril et al. |
| 2004/0223778 A1 | 11/2004 | Zwiefelhofer |
| 2004/0226993 A1 | 11/2004 | Fulcher et al. |
| 2004/0227968 A1 | 11/2004 | Nakamura et al. |
| 2004/0230500 A1 | 11/2004 | Imago |
| 2004/0236862 A1 | 11/2004 | Ito |
| 2004/0254955 A1 | 12/2004 | Reese et al. |
| 2004/0255263 A1 | 12/2004 | Ando |
| 2004/0268229 A1 | 12/2004 | Paoli et al. |
| 2004/0268306 A1 | 12/2004 | Cheng et al. |
| 2005/0005094 A1 | 1/2005 | Jamieson et al. |
| 2005/0009187 A1 | 1/2005 | Shinozaki et al. |
| 2005/0015472 A1 | 1/2005 | Catania et al. |
| 2005/0015585 A1 | 1/2005 | Kurose |
| 2005/0026593 A1 | 2/2005 | Anderson et al. |
| 2005/0028086 A1 | 2/2005 | Itavaara et al. |
| 2005/0044248 A1 | 2/2005 | Mihira et al. |
| 2005/0055475 A1 | 3/2005 | MacKay et al. |
| 2005/0057560 A1 | 3/2005 | Bibr et al. |
| 2005/0060046 A1 | 3/2005 | Ito et al. |
| 2005/0060564 A1 | 3/2005 | Murakami et al. |
| 2005/0063010 A1 | 3/2005 | Giannetti |
| 2005/0068581 A1 | 3/2005 | Hull et al. |
| 2005/0071507 A1 | 3/2005 | Ferlitsch |
| 2005/0071746 A1 | 3/2005 | Hart et al. |
| 2005/0080649 A1 | 4/2005 | Alvarez et al. |
| 2005/0091087 A1 | 4/2005 | Smith et al. |
| 2005/0091490 A1 | 4/2005 | Ogura |
| 2005/0097458 A1 | 5/2005 | Wilson |
| 2005/0108353 A1 | 5/2005 | Yamamoto |
| 2005/0114267 A1 | 5/2005 | Miwa et al. |
| 2005/0114658 A1 | 5/2005 | Dye et al. |
| 2005/0114766 A1 | 5/2005 | Yamamoto |
| 2005/0129423 A1 | 6/2005 | Lester et al. |
| 2005/0149576 A1 | 7/2005 | Marmaros et al. |
| 2005/0152334 A1 | 7/2005 | Okamoto et al. |
| 2005/0185217 A1 | 8/2005 | Nishizawa et al. |
| 2005/0195221 A1 | 9/2005 | Berger et al. |
| 2005/0223413 A1 | 10/2005 | Duggan et al. |
| 2005/0231755 A1 | 10/2005 | Araumi et al. |
| 2005/0246428 A1 | 11/2005 | Araumi |
| 2005/0257134 A1 | 11/2005 | Goodman et al. |
| 2005/0257148 A1 | 11/2005 | Goodman et al. |
| 2005/0265744 A1 | 12/2005 | Uruta |
| 2006/0007480 A1 | 1/2006 | Yokokura |

| | | | | | | |
|---|---|---|---|---|---|---|
| 2006/0010180 | A1* | 1/2006 | Kawamura et al. ............ 707/204 | JP | 2004246771 | 9/2004 |
| 2006/0015734 | A1 | 1/2006 | Atobe | JP | 2004310326 | 11/2004 |
| 2006/0028397 | A1 | 2/2006 | O'Rourke | JP | 2004310516 | 11/2004 |
| 2006/0031411 | A1 | 2/2006 | Gimson et al. | JP | 2004276271 | 12/2004 |
| 2006/0038004 | A1 | 2/2006 | Rielly et al. | JP | 2004358800 | 12/2004 |
| 2006/0056873 | A1 | 3/2006 | Kimura | JP | 2005014591 | 1/2005 |
| 2006/0059434 | A1 | 3/2006 | Boss et al. | JP | 2005033460 | 2/2005 |
| 2006/0064647 | A1 | 3/2006 | Tapuska et al. | JP | 2005059496 | 3/2005 |
| 2006/0077423 | A1 | 4/2006 | Mathieson et al. | JP | 2005078278 | 3/2005 |
| 2006/0077432 | A1 | 4/2006 | Lovat et al. | JP | 2005084891 | 3/2005 |
| 2006/0077439 | A1 | 4/2006 | Yamamura et al. | JP | 2005115543 | 4/2005 |
| 2006/0077444 | A1 | 4/2006 | Lum et al. | JP | 2005004243 | 6/2005 |
| 2006/0085835 | A1 | 4/2006 | Istvan et al. | JP | 2005209059 | 8/2005 |
| 2006/0112123 | A1 | 5/2006 | Clark et al. | JP | 2005219440 A | 8/2005 |
| 2006/0154227 | A1 | 7/2006 | Rossi et al. | JP | 2005235034 A | 9/2005 |
| 2006/0162076 | A1 | 7/2006 | Bartlett et al. | JP | 2005269250 | 9/2005 |
| 2006/0198653 | A1 | 9/2006 | Plewnia et al. | JP | 2006053905 | 2/2006 |
| 2006/0224405 | A1 | 10/2006 | White et al. | JP | 2006140898 | 6/2006 |
| 2006/0279475 | A1 | 12/2006 | Lum et al. | WO | WO0118754 A1 | 3/2001 |
| 2007/0022180 | A1 | 1/2007 | Cocotis et al. | WO | WO01/33381 | 5/2001 |
| 2007/0041035 | A1 | 2/2007 | Sembower et al. | WO | WO0198864 | 12/2001 |
| 2007/0094103 | A1 | 4/2007 | Hyakutake et al. | | | |
| 2007/0173266 | A1 | 7/2007 | Barnes, Jr. | | | |
| 2007/0174894 | A1 | 7/2007 | Matsunaga | | | |
| 2007/0186150 | A1 | 8/2007 | Rao et al. | | | |
| 2008/0072162 | A1 | 3/2008 | Dauerer et al. | | | |

FOREIGN PATENT DOCUMENTS

| | | |
|---|---|---|
| JP | 09160441 | 12/1995 |
| JP | 08234945 | 9/1996 |
| JP | 09293036 | 11/1997 |
| JP | 09330190 | 12/1997 |
| JP | 10013695 | 1/1998 |
| JP | 10154190 A | 6/1998 |
| JP | 10240490 | 9/1998 |
| JP | 10269184 | 10/1998 |
| JP | 2000112691 | 4/2000 |
| JP | 2000174949 | 6/2000 |
| JP | 2000207108 | 7/2000 |
| JP | 2002259071 | 2/2001 |
| JP | 2001268296 | 9/2001 |
| JP | 200284383 | 3/2002 |
| JP | 2002140195 | 5/2002 |
| JP | 2002175195 | 6/2002 |
| JP | 2002221877 | 8/2002 |
| JP | 2002236830 | 8/2002 |
| JP | 2002298049 A | 10/2002 |
| JP | 2002312148 | 10/2002 |
| JP | 2002330253 | 11/2002 |
| JP | 2002351644 | 12/2002 |
| JP | 2003022258 | 1/2003 |
| JP | 2003050781 | 2/2003 |
| JP | 2003157155 A | 5/2003 |
| JP | 2003178023 | 6/2003 |
| JP | 2003196554 A | 7/2003 |
| JP | 2003198792 | 7/2003 |
| JP | 2003208484 | 7/2003 |
| JP | 2003209644 | 7/2003 |
| JP | 2003216368 | 7/2003 |
| JP | 2003216395 A | 7/2003 |
| JP | 2003223299 | 8/2003 |
| JP | 2003260853 | 9/2003 |
| JP | 2003281227 | 10/2003 |
| JP | 2003288179 | 10/2003 |
| JP | 2003308195 | 10/2003 |
| JP | 200430448 | 1/2004 |
| JP | 2004074530 | 3/2004 |
| JP | 2004088561 | 3/2004 |
| JP | 2004094313 | 3/2004 |
| JP | 2004128561 | 4/2004 |
| JP | 2004118549 | 5/2004 |
| JP | 2004164157 A | 6/2004 |
| JP | 2004185396 | 7/2004 |
| JP | 2004213356 | 7/2004 |
| JP | 2004215309 | 7/2004 |
| JP | 2004222247 | 8/2004 |
| JP | 2004228686 | 8/2004 |
| JP | 2004228687 | 8/2004 |
| JP | 2004240752 | 8/2004 |

OTHER PUBLICATIONS

R. Herriot, Internet Printing Protocol (IPP): Event Notifications and Subscriptions (Feb. 21, 2003, retrieved from http://tools.ietf.org/html/draft-ietf-ipp-not-spec-11 on Aug. 20, 2008, pp. 1-101).

T. Hastings, "Internet Printing Protocol/1.1: Model and Semantics" (Sep. 2000, retrieved from http://www.ietf.org/rfc/rfc291.txt on Sep. 18, 2008, pp. 1-210).

R. Herriot, Internet Printing Protocol (IPP): Event Notifications and Subscriptions, Jun. 21, 2004, http://tools.ietf.org/html/draft-ietf-ipp-not-spec-12, pp. 1-98.

Microsoft Corporation. Microsoft Computer Dictionary, Fifth Edition, 2002 Microsoft Press, pp. 487-488.

Gaedke, Martin et al. "A Modeling Approach to Federated Identity and Access Management", May 2005 ACM.

FOLDOC. "relational database", Jun. 2002, retrieved from <http://foldoc.org/index.cgi?query=relational+database>.

Oasis. "Security Assertion Markup Language (SAML) 2.0 Technical Overview", Working Draft 01, Jul. 22, 2004, <http://www.oasis-open.org/committees/documents.php?wg_abbrev=security>.

Hartman, Bret et al. Mastering Web Services Security, 2003 Wiley Publishing, Inc., pp. 36-46.

U.S. Appl. No. 10/962,248—Office Action dated Aug. 19, 2008.
U.S. Appl. No. 10/961,793—Office Action dated Jun. 20, 2008.
U.S. Appl. No. 10/961,793—Office Action dated Dec. 19, 2008.
U.S. Appl. No. 10/961,911—Office Action dated Oct. 28, 2008.
U.S. Appl. No. 10/961,594—Office Action dated Dec. 3, 2008.
U.S. Appl. No. 10/961,594—Office Action dated Mar. 16, 2009.
U.S. Appl. No. 10/962,103—Office Action dated Jul. 9, 2008.
U.S. Appl. No. 10/962,103—Office Action dated Jan. 23, 2009.
U.S. Appl. No. 11/232,827—Office Action dated Dec. 5, 2008.
U.S. Appl. No. 11/073,055—Office Action dated Sep. 18, 2008.
U.S. Appl. No. 11/073,055—Office Action dated Mar. 4, 2009.
U.S. Appl. No. 11/233,202—Office Action dated Jun. 5, 2008.
U.S. Appl. No. 11/233,202—Office Action dated Dec. 1, 2008.
U.S. Appl. No. 11/233,201—Office Action dated Oct. 3, 2008.
U.S. Appl. No. 11/232,552—Office Action dated Nov. 18, 2008.
U.S. Appl. No. 11/233,270—Office Action dated Sep. 17, 2008.
U.S. Appl. No. 11/241,501—Office Action dated Oct. 23, 2008.
U.S. Appl. No. 11/241,497—Office Action dated Feb. 20, 2009.
U.S. Appl. No. 11/241,497—Office Action dated Aug. 27, 2008.
U.S. Appl. No. 11/241,011—Office Action dated Oct. 8, 2008.
U.S. Appl. No. 11/241,010—Office Action dated Oct. 9, 2008.
U.S. Appl. No. 11/241,071—Office Action dated Mar. 3, 2009.
U.S. Appl. No. 11/241,071—Office Action dated Sep. 19, 2008.
U.S. Appl. No. 11/241,447—Office Action dated Mar. 5, 2009.
U.S. Appl. No. 11/241,447—Office Action dated Sep. 15, 2008.
U.S. Appl. No. 11/241,498—Office Action dated Sep. 16, 2008.
U.S. Appl. No. 11/241,498—Office Action dated Mar. 5, 2009.
U.S. Appl. No. 11/240,039—Office Action dated Oct. 20, 2008.
U.S. Appl. No. 11/240,156—Office Action dated Aug. 28, 2008.
U.S. Appl. No. 11/240,156—Office Action dated Feb. 20, 2009.
U.S. Appl. No. 11/255,611—Office Action dated Mar. 12, 2009.

U.S. Appl. No. 11/256,479—Office Action dated Nov. 4, 2008.
U.S. Appl. No. 11/255,333—Office Action dated Mar. 13, 2009.
U.S. Appl. No. 11/193,154—Office Action dated Dec. 2, 2008.
U.S. Appl. No. 11/192,630—Office Action dated Jan. 21, 2009.
U.S. Appl. No. 11/192,546—Office Action dated Jan. 22, 2009.
U.S. Appl. No. 11/192,836—Office Action dated Jul. 9, 2008.
U.S. Appl. No. 11/193,147—Office Action dated Jul. 9, 2008.
U.S. Appl. No. 11/192,868—Office Action dated Feb. 2, 2009.
U.S. Appl. No. 11/192,629—Office Action dated Jan. 22, 2009.
U.S. Appl. No. 11/193,151—Office Action dated Feb. 23, 2009.
U.S. Appl. No. 11/193,188—Office Action dated Jan. 21, 2009.
U.S. Appl. No. 11/193,140—Office Action dated Nov. 18, 2008.
U.S. Appl. No. 11/192,796—Office Action dated Feb. 24, 2009.
U.S. Appl. No. 11/192,547—Office Action dated Feb. 5, 2009.
U.S. Appl. No. 11/240,084—Office Action dated Oct. 30, 2008.
U.S. Appl. No. 11/218,033—Office Action dated Sep. 12, 2008.
U.S. Appl. No. 10/961,911—Office Action dated Apr. 16, 2008.
U.S. Appl. No. 10/961,594—Office Action dated Jan. 7, 2008.
U.S. Appl. No. 11/193,077—Office Action dated Apr. 6, 2007.
U.S. Appl. No. 11/192,836—Office Action dated Dec. 5, 2007.
U.S. Appl. No. 11/192,836—Office Action dated Jul. 3, 2007.
U.S. Appl. No. 11/192,836—Office Action dated Jan. 30, 2007.
U.S. Appl. No. 11/193,147—Office Action dated Dec. 6, 2007.
U.S. Appl. No. 11/193,147—Office Action dated Jul. 23, 2007.
U.S. Appl. No. 11/193,147—Office Action dated Feb. 9, 2007.
Canon USA, Inc.; MEAP Multifunctional Embedded Application Platform; Aug. 2004; http://developersupport.canon.com/Web_MEAP_Presentation.pdf.
Canon USA, Inc.; MEAP: FAQ; accessed on Jul. 2004, pub. date unknown; http://developersupport.canon.com/MEAP.htm.
XEROX, Inc.; XEROX FreeFlow digital workflow collection; 2003; http://www.xerox.com/downloads/usa/en/s/solutions_digital_workflow_whitepaper_sdk.pdf.
Ricoh Company, LTD.; Ricoh's Medium-Term Management Plan; Mar. 19, 2002; http://www.ricoh.com/IR/data/pre/pdf/ir_pre2002.pdf.
Ricoh Company, LTD.; White Paper: Embedded Software Architecture SDK; Jun. 25, 2003. http://www.ricoh-usa.com/products/concept/esa.asp?catname=ESA.
Hewlett-Packard Company; JetCAPS Scan2Folder, 2003; http://www.jetcaps.se/resources/datasheets/ds_scan2folder.pdf.
Hewlett-Packard Company; JetCAPS chai applications; Dec. 9, 2002; http://www.stethos.com/chai/data/d_us_chai.pdf.
Ratha, N. K., Connell, J.H., Bolle, R.M. "Enhancing security and privacy in biometrics-based authentication systems". IBM Systems Journal 40(3), pp. 614-634 (2001).
U.S. Appl. No. 10/962,248—Final Office Action dated Jun. 10, 2009.
U.S. Appl. No. 10/962,248—Non-Final Office Action dated Jan. 29, 2010.
U.S. Appl. No. 11/232,588—Non-Final Office Action dated Apr. 1, 2009.
U.S. Appl. No. 11/232,588—Final Office Action dated Nov. 27, 2009.
U.S. Appl. No. 10/961,793—Non-Final Office Action dated Jun. 24, 2009.
U.S. Appl. No. 10/961,793—Final Office Action dated Feb. 4, 2010.
U.S. Appl. No. 10/961,911—Non-Final Office Action dated Jun. 8, 2009.
U.S. Appl. No. 10/961,911—Non-Final Office Action dated Feb. 3, 2010.
U.S. Appl. No. 10/962,103—Non-Final Office Action dated Aug. 14, 2009.
U.S. Appl. No. 11/232,827—Final Office Action dated Jun. 4, 2009.
U.S. Appl. No. 11/232,827—Non-Final Office Action dated Dec. 1, 2009.
U.S. Appl. No. 11/073,055—Non-Final Office Action dated Jun. 19, 2009.
U.S. Appl. No. 11/073,055—Final Office Action dated Feb. 18, 2010.
U.S. Appl. No. 11/233,202—Non-Final Office Action dated Jun. 9, 2009.
U.S. Appl. No. 11/233,202—Final Office Action dated Jan. 15, 2010.
U.S. Appl. No. 11/233,201—Final Office Action dated Apr. 28, 2009.
U.S. Appl. No. 11/233,201—Non-Final Office Action dated Sep. 4, 2009.
U.S. Appl. No. 11/232,552—Final Office Action dated Jun. 24, 2009.
U.S. Appl. No. 11/232,552—Non-Final Office Action dated Dec. 24, 2009.
U.S. Appl. No. 11/233,270—Final Office Action dated Mar. 31, 2009.
U.S. Appl. No. 11/233,270—Final Office Action dated Nov. 27, 2009.
U.S. Appl. No. 11/465,699—Non-Final Office Action dated Sep. 17, 2008.
U.S. Appl. No. 11/465,699—Final Office Action dated Mar. 31, 2009.
U.S. Appl. No. 11/465,699—Final Office Action dated Nov. 27, 2009.
U.S. Appl. No. 11/465,722—Non-Final Office Action dated Dec. 24, 2009.
U.S. Appl. No. 11/241,501—Final Office Action dated May 13, 2009.
U.S. Appl. No. 11/241,501—Non-Final Office Action dated Feb. 9, 2010.
U.S. Appl. No. 11/241,497—Non-Final Office Action dated Oct. 6, 2009.
U.S. Appl. No. 11/241,011—Final Office Action dated Apr. 2, 2009.
U.S. Appl. No. 11/241,011—Non-Final Office Action dated Jan. 4, 2010.
U.S. Appl. No. 11/241,010—Final Office Action dated Mar. 20, 2009.
U.S. Appl. No. 11/241,071—Non-Final Office Action dated Aug. 19, 2009.
U.S. Appl. No. 11/241,447—Non-Final Office Action dated Jul. 22, 2009.
U.S. Appl. No. 11/241,498—Non-Final Office Action dated Dec. 10, 2009.
U.S. Appl. No. 11/240,039—Final Office Action dated Apr. 13, 2009.
U.S. Appl. No. 11/240,039—Non-Final Office Action dated Nov. 3, 2009.
U.S. Appl. No. 11/240,156—Non-Final Office Action dated Sep. 16, 2009.
U.S. Appl. No. 11/255,611—Notice of Allowance dated Aug. 10, 2009.
U.S. Appl. No. 11/256,479—Final Office Action dated Apr. 1, 2009.
U.S. Appl. No. 11/256,479—Non-Final Office Action dated Nov. 16, 2009.
U.S. Appl. No. 11/192,617—Non-Final Office Action dated Sep. 29, 2009.
U.S. Appl. No. 11/193,154—Non-Final Office Action dated Jun. 3, 2009.
U.S. Appl. No. 11/193,154—Final Office Action dated Dec. 7, 2009.
U.S. Appl. No. 11/192,630—Final Office Action dated Sep. 2, 2009.
U.S. Appl. No. 11/192,546—Final Office Action dated Jun. 30, 2009.
U.S. Appl. No. 11/192,546—Non-Final Office Action dated Nov. 24, 2009.
U.S. Appl. No. 11/193,077—Notice of Allowance dated Mar. 11, 2008.
U.S. Appl. No. 11/192,870—Non-Final Office Action dated Jul. 17, 2009.
U.S. Appl. No. 11/192,870—Final Office Action dated Jan. 4, 2010.
U.S. Appl. No. 11/192,836—Notice of Allowance dated Dec. 30, 2008.
U.S. Appl. No. 11/192,616—Non-Final Office Action dated Sep. 17, 2009.
U.S. Appl. No. 11/193,147—Notice of Allowance dated Dec. 30, 2008.
U.S. Appl. No. 11/192,868—Final Office Action dated Aug. 11, 2009.
U.S. Appl. No. 11/192,629—Final Office Action dated Jun. 26, 2009.
U.S. Appl. No. 11/192,629—Non-Final Office Action dated Jan. 15, 2010.
U.S. Appl. No. 11/193,151—Final Office Action dated Sep. 21, 2009.
U.S. Appl. No. 11/193,188—Final Office Action dated Aug. 5, 2009.
U.S. Appl. No. 11/192,824—Non-Final Office Action dated Sep. 18, 2009.

U.S. Appl. No. 11/193,140—Final Office Action dated May 18, 2009.
U.S. Appl. No. 11/193,140—Notice of Allowance dated Jan. 29, 2010.
U.S. Appl. No. 11/192,796—Non-Final Office Action dated Dec. 28, 2009.
U.S. Appl. No. 11/192,615—Non-Final Office Action dated Sep. 4, 2009.
U.S. Appl. No. 11/192,547—Final Office Action dated Jan. 15, 2010.
U.S. Appl. No. 11/192,467—Non-Final Office Action dated Nov. 13, 2009.
U.S. Appl. No. 11/255,333—Notice of Allowance dated Nov. 3, 2009.
U.S. Appl. No. 11/465,747—Non-Final Office Action dated Jun. 24, 2009.
U.S. Appl. No. 11/465,752—Non-Final Office Action dated Jun. 24, 2009.
U.S. Appl. No. 11/241,320—Non-Final Office Action dated Oct. 7, 2009.
U.S. Appl. No. 11/240,139—Non-Final Office Action dated Oct. 6, 2009.
U.S. Appl. No. 11/240,084—Final Office Action dated Apr. 15, 2009.
U.S. Appl. No. 11/240,084—Non-Final Office Action dated Dec. 16, 2009.
U.S. Appl. No. 11/218,033—Final Office Action dated Mar. 30, 2009.
U.S. Appl. No. 11/218,033—Non-Final Office Action dated Sep. 8, 2009.
U.S. Appl. No. 11/218,186—Non-Final Office Action dated Jun. 23, 2009.
U.S. Appl. No. 11/218,186—Final Office Action dated Feb. 1, 2010.
U.S. Appl. No. 11/562,342—Non-Final Office Action dated May 29, 2009.
U.S. Appl. No. 11/562,342—Final Office Action dated Dec. 21, 2009.
U.S. Appl. No. 11/685,046—Non-Final Office Action dated Jul. 8, 2009.
U.S. Appl. No. 11/685,046—Final Office Action dated Dec. 21, 2009.
JP Patent App. No. 2006-261563—Office Action filed for a related foreign application dated Jan. 19, 2010.
JP Patent App. No. 2006-207199—Office Action filed for a related foreign application dated Feb. 2, 2010.
JP Patent App. No. 2006-058600—Office Action filed for a related foreign application dated Aug. 18, 2009.
JP Patent App. No. 2005-295772—Office Action filed for a related foreign application dated Sep. 15, 2009.
JP Patent App. No. 2005-295772—Notice of Allowance filed for a related foreign application dated Dec. 15, 2009.
JP Patent App. No. 2006-207200—Office Action filed for a related foreign application dated Feb. 2, 2010.
JP Patent App. No. 2006-207194—Office Action filed for a related foreign application dated Jan. 12, 2010.
JP Patent App. No. 2006-261564—Office Action filed for a related foreign application dated Jan. 19, 2010.
JP Patent App. No. 2006-207199—Office Action filed for a related foreign application dated Nov. 17, 2009.
JP Patent App. No. 2007-225913—Office Action filed for a related foreign application dated Dec. 24, 2009.
JP Patent App. No. 2006-256442—Office Action filed for a related foreign application dated Jul. 14, 2009.
JP Patent App. No. 2006-207194—Office Action filed for a related foreign application dated Jun. 23, 2009.
Foreign Patent App. No. JP2006-058600—Office Action filed for a related foreign application dated Aug. 18, 2009 corresponding to U.S. Appl. No. 11/073,055.
Foreign Patent App. No. JP2006-207200—Office Action filed for a related foreign application dated Jun. 1, 2010 corresponding to U.S. Appl. No. 11/192,547.
Foreign Patent App. No. JP2006-207196—Office Action filed for a related foreign application dated Mar. 2, 2010 corresponding to U.S. Appl. No. 11/192,862.
Foreign Patent App. No. JP2006-256441—Office Action filed for a related foreign application dated Mar. 30, 2010 corresponding to U.S. Appl. No. 11/233,202.
Foreign Patent App. No. JP2006-207198—Office Action filed for a related foreign application dated Mar. 2, 2010 corresponding to U.S. Appl. No. 11/192,616.
U.S. Appl. No. 10/961,594—Final Office Action dated Apr. 2, 2010.
U.S. Appl. No. 10/962,103—Non-final Office Action dated May 14, 2010.
U.S. Appl. No. 11/232,827—Final Office Action dated Jun. 14, 2010.
U.S. Appl. No. 11/233,201—Final Office Action dated Jun. 3, 2010.
U.S. Appl. No. 11/232,588—Notice of Allowance dated Jun. 23, 2010.
U.S. Appl. No. 11/233,270—Non-final Office Action dated Jun. 9, 2010.
U.S. Appl. No. 11/465,699—Non-final Office Action dated Nov. 16, 2009.
U.S. Appl. No. 11/465,699—Final Office Action dated May 24, 2010.
U.S. Appl. No. 11/465,722—Final Office Action dated Apr. 30, 2010.
U.S. Appl. No. 11/241,011—Final Office Action dated Jun. 29, 2010.
U.S. Appl. No. 11/241,010—Non-final Office Action dated Apr. 15, 2010.
U.S. Appl. No. 11/241,071—Final Office Action dated Apr. 16, 2010.
U.S. Appl. No. 11/241,447—Final Office Action dated Apr. 1, 2010.
U.S. Appl. No. 11/240,039—Notice of Allowance dated Jun. 3, 2010.
U.S. Appl. No. 11/240,156—Final Office Action dated Mar. 31, 2010.
U.S. Appl. No. 11/256,479—Final Office Action dated May 13, 2010.
U.S. Appl. No. 11/192,617—Final Office Action dated Jun. 11, 2010.
U.S. Appl. No. 11/193,076—Non-final Office Action dated Apr. 5, 2010.
U.S. Appl. No. 11/192,630—Non-final Office Action dated Apr. 9, 2010.
U.S. Appl. No. 11/192,546—Final Office Action dated Jul. 14, 2010.
U.S. Appl. No. 11/192,937—First Action Interview Pilot Program Pre-Interview Communication dated Apr. 7, 2010.
U.S. Appl. No. 11/192,616—Final Office Action dated May 26, 2010.
U.S. Appl. No. 11/192,500—Non-final Office Action dated Jul. 21, 2010.
U.S. Appl. No. 11/192,868—Non-final Office Action dated May 19, 2010.
U.S. Appl. No. 11/193,188—Non-final Office Action dated Apr. 19, 2010.
U.S. Appl. No. 11/192,824—Non-final Office Action dated Mar. 1, 2010.
U.S. Appl. No. 11/192,615—Final Office Action dated Apr. 20, 2010.
U.S. Appl. No. 11/192,547—Non-final Office Action dated Jun. 25, 2010.
U.S. Appl. No. 11/192,467—Final Office Action dated Jun. 25, 2010.
U.S. Appl. No. 11/256,493—Non-final Office Action dated Mar. 9, 2010.
U.S. Appl. No. 11/465,752—Final Office Action dated Apr. 2, 2010.
U.S. Appl. No. 11/241,320—Final Office Action dated Jun. 17, 2010.
U.S. Appl. No. 11/240,139—Final Office Action dated Jun. 9, 2010.
U.S. Appl. No. 11/536,115—Non-final Office Action dated Jun. 15, 2010.
U.S. Appl. No. 11/218,033—Final Office Action dated May 14, 2010.
Foreign Patent App. No. JP2006205150—Office Action filed for a related foreign application dated Sep. 28, 2010 corresponding to U.S. Appl. No. 11/192,500.
Foreign Patent App. No. JP2006207198—Office Action filed for a related foreign application dated Sep. 21, 2010 corresponding to U.S. Appl. No. 11/192,836.
Foreign Patent App. No. JP2006256441—Office Action filed for a related foreign application dated Nov. 9, 2010 corresponding to U.S. Appl. No. 11/233,202.
Foreign Patent App. No. JP2006256440—Office Action filed for a related foreign application dated Oct. 19, 2010 corresponding to U.S. Appl. No. 11/233,270.

U.S. Appl. No. 10/961,793—Non-Final Office Action dated Oct. 28, 2010.
U.S. Appl. No. 10/961,911—Final Office Action dated Oct. 20, 2010.
U.S. Appl. No. 11/073,055—Non-Final Office Action dated Nov. 23, 2010.
U.S. Appl. No. 11/233,270—Notice of Allowance dated Nov. 30, 2010.
U.S. Appl. No. 11/241,010—Final Office Action dated Oct. 15, 2010.
U.S. Appl. No. 11/240,156—Non-Final Office Action dated Nov. 10, 2010.
U.S. Appl. No. 11/256,479—Non-Final Office Action dated Nov. 23, 2010.
U.S. Appl. No. 11/193,152—Non-Final Office Action dated Mar. 1, 2010.
U.S. Appl. No. 11/193,152—Final Office Action dated Nov. 18, 2010.
U.S. Appl. No. 11/193,151—Non-Final Office Action dated Mar. 29, 2010.
U.S. Appl. No. 11/193,151—Final Office Action dated Nov. 2, 2010.
U.S. Appl. No. 11/192,824—Final Office Action dated Oct. 22, 2010.
U.S. Appl. No. 11/465,747—Final Office Action dated Mar. 9, 2010.
U.S. Appl. No. 11/241,447—Non-Final Office Action dated Dec. 8, 2010.
U.S. Appl. No. 11/193,076—Final Office Action dated Jan. 6, 2011.
U.S. Appl. No. 11/192,630—Final Office Action dated Dec. 8, 2010.
U.S. Appl. No. 11/192,868—Final Office Action dated Dec. 8, 2010.
U.S. Appl. No. 11/193,188—Final Office Action dated Dec. 8, 2010.
U.S. Appl. No. 11/192,615—Non-Final Office Action dated Jan. 4, 2011.
U.S. Appl. No. 11/192,467—Notice of Allowance dated Dec. 22, 2010.
U.S. Appl. No. 11/465,747—Notice of Allowance dated Dec. 28, 2010.
E. Uemukai Toshiaki, A WWW Browsing System in Remote Display Environments, IPSJ magazine, Information Processing Society of Japan, Publication Date: Sep. 15, 2000, vol. 41, No. 9, p. 2364 to 2373.
Foreign Patent App. No. JP2006256440—Office Action filed for a related foreign application dated Jun. 7, 2010 corresponding to U.S. Appl. No. 11/233,270.
Foreign Patent App. No. JP2006261564—Office Action filed for a related foreign application dated Jun. 15, 2010 corresponding to U.S. Appl. No. 11/241,010.
Foreign Patent App. No. JP2006207195—Office Action filed for a related foreign application dated Jul. 27, 2010 corresponding to U.S. Appl. No. 11/192,617.
U.S. Appl. No. 10/962,248—Final Office Action dated Aug. 17, 2010.
U.S. Appl. No. 10/961,594—Non-Final Office Action dated Sep. 15, 2010.
U.S. Appl. No. 11/233,202—Non-Final Office Action dated Jul. 27, 2010.
U.S. Appl. No. 11/233,201—Non-Final Office Action dated Sep. 15, 2010.
U.S. Appl. No. 11/232,552—Final Office Action dated Aug. 19, 2010.
U.S. Appl. No. 11/241,501—Final Office Action dated Jul. 22, 2010.
U.S. Appl. No. 11/241,497—Notice of Allowance dated Aug. 11, 2010.
U.S. Appl. No. 11/241,498—Final Office Action dated Jul. 22, 2010.
U.S. Appl. No. 11/192,862—Non-Final Office Action dated Jul. 26, 2010.
U.S. Appl. No. 11/192,937—Notice of Allowance dated Sep. 7, 2010.
U.S. Appl. No. 11/192,629—Final Office Action dated Aug. 25, 2010.
U.S. Appl. No. 11/192,796—Notice of Allowance dated Sep. 10, 2010.
U.S. Appl. No. 11/256,493—Final Office Action dated Aug. 20, 2010.
U.S. Appl. No. 11/240,084—Final Office Action dated Aug. 6, 2010.

* cited by examiner

METHODS AND SYSTEMS FOR IMAGING DEVICE ACCOUNTING DATA MAINTENANCE

RELATED REFERENCES

This application is a continuation-in-part of U.S. patent application Ser. No. 10/962,248, entitled "Methods and Systems for Imaging Device Remote Application Interaction, filed on Oct. 8, 2004; this application is also a continuation-in-part of U.S. patent application Ser. No. 10/961,793, entitled "Methods and Systems for Imaging Device Remote Form Management, filed on Oct. 8, 2004; this application is also a continuation-in-part of U.S. patent application Ser. No. 10/961,911, entitled "Methods and Systems for Imaging Device Remote Location Functions, filed on Oct. 8, 2004; this application is also a continuation-in-part of U.S. patent application Ser. No. 10/961,594, entitled "Methods and Systems for Imaging Device Remote document Management, filed on Oct. 8, 2004; and this application is also a continuation-in-part of U.S. patent application Ser. No. 10/962,103, entitled "Methods and Systems for Imaging Device Document Translation, filed on Oct. 8, 2004; this application also claims the benefit of U.S. Provisional Patent Application No. 60/704,066, entitled "Methods and Systems for Imaging Device Applications," filed Jul. 28, 2005.

FIELD OF THE INVENTION

Embodiments of the present invention comprise methods and systems for preserving imaging device (IDev) accounting data when an imaging system's main accounting server becomes unavailable.

BACKGROUND

Imaging devices such as printers, copiers, scanners and fax machines can have a wide array of functions and capabilities to fit specific uses or combinations of uses. Imaging devices often take the form of a multi-function peripheral device (MFP) that combines the functions of two or more of the traditionally separated imaging devices. An MFP may combine any number of imaging devices, but typically comprises the functions of a printer, scanner, copier and fax machine.

Some imaging devices may contain computing resources for data storage and processing such as processors, hard disk drives, memory and other devices. As imaging devices add more features and functions, they become more costly and complex.

More complex imaging devices and MFPs may comprise network connectivity to provide communication with other computing devices, such as personal computers, other imaging devices, network servers and other apparatus. This connectivity allows the imaging device to utilize off-board resources that are available on a connected network.

Imaging devices typically have a user input panel with an array of buttons, knobs and other user input devices. Some devices also have a display panel, which can be for display only or can be a touch panel display that enables user input directly on the display.

Devices with touch panel displays or displays with buttons arranged in cooperation with the display can display menu data that may be selected by user input. This menu data is typically driven by an on-board server module within the imaging device.

BRIEF SUMMARY OF THE INVENTION

Embodiments of the present invention comprise methods and systems for the continuous capture of accounting data when an imaging system's main accounting server becomes unavailable.

The foregoing and other objectives, features, and advantages of the invention will be more readily understood upon consideration of the following detailed description of the invention taken in conjunction with the accompanying drawings.

BRIEF DESCRIPTION OF THE SEVERAL DRAWINGS

DETAILED DESCRIPTION OF EXEMPLARY EMBODIMENTS

Figure 1:
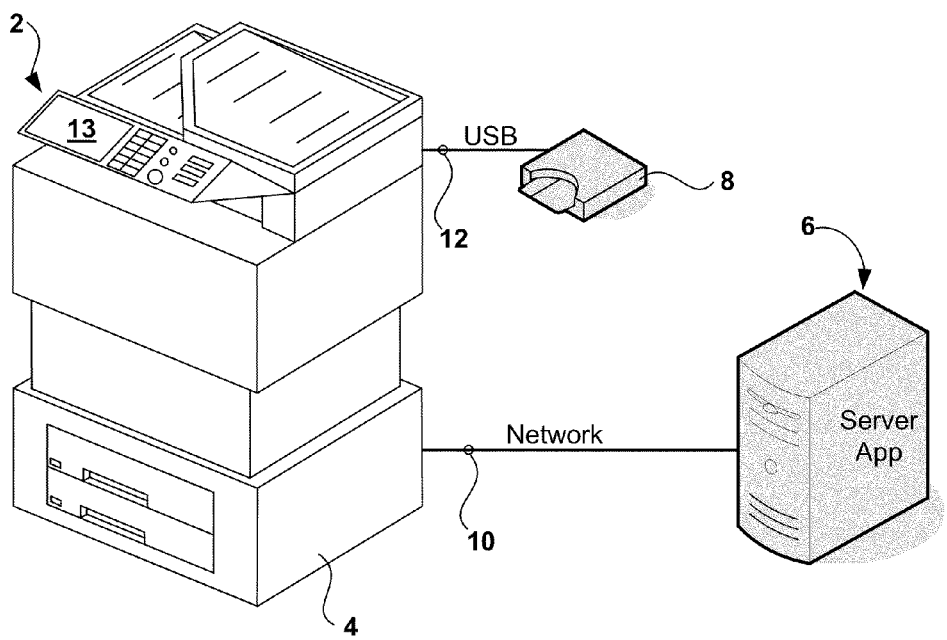
FIG. 1 is a diagram of an embodiment of the present invention comprising an imaging device in connection with a remote computing device.

Embodiments of the present invention will be best understood by reference to the drawings, wherein like parts are designated by like numerals throughout. The figures listed above are expressly incorporated as part of this detailed description.

It will be readily understood that the components of the present invention, as generally described and illustrated in the figures herein, could be arranged and designed in a wide variety of different configurations. Thus, the following more detailed description of the embodiments of the methods and systems of the present invention is not intended to limit the scope of the invention but it is merely representative of the presently preferred embodiments of the invention.

Elements of embodiments of the present invention may be embodied in hardware, firmware and/or software. While exemplary embodiments revealed herein may only describe one of these forms, it is to be understood that one skilled in the art would be able to effectuate these elements in any of these forms while resting within the scope of the present invention.

Embodiments of the present invention comprise interfaces and architecture that integrate imaging devices with remote computing device applications and environments to provide solutions that may not be possible solely with an imaging device alone. Some embodiments comprise an infrastructure and set of interfaces that allow applications on a network to programmatically control imaging device functions and interact with a user through an imaging device input panel. Software functions that are not practical within the imaging device can be performed on the server but are accessible from the imaging device.

For the purposes of this specification and claims, an imaging device (IDev) may be described as a device that performs an imaging function. Imaging functions comprise scanning, printing, copying, image transmission (sending and receiving), image conversion and other functions. Exemplary imaging devices comprise printers, copiers, facsimile machines, scanners, computing devices that transmit, convert or process images and other devices. An IDev may also perform multiple imaging functions. For example, and not by way of limitation, a multi-function peripheral device (MFP), which typically has the capability to perform a plurality of functions comprising a printer, scanner, copier and/or a facsimile machine or image transmitter/receiver, is a type of imaging device. Other MFP imaging devices may comprise other combinations of functions and still qualify as an IDev.

For the purposes of this specification and claims, a remote computing device (RCD) is a device capable of processing data and communicating with other devices through a communications link. An RCD is a remote device because it requires a communications link, such as a network connection, a telephone line, a serial cable or some other wired or wireless link to communicate with other devices such as an imaging device. Some exemplary RCDs are network servers, networked computers and other processing and storage devices that have communications links.

Figure 2:
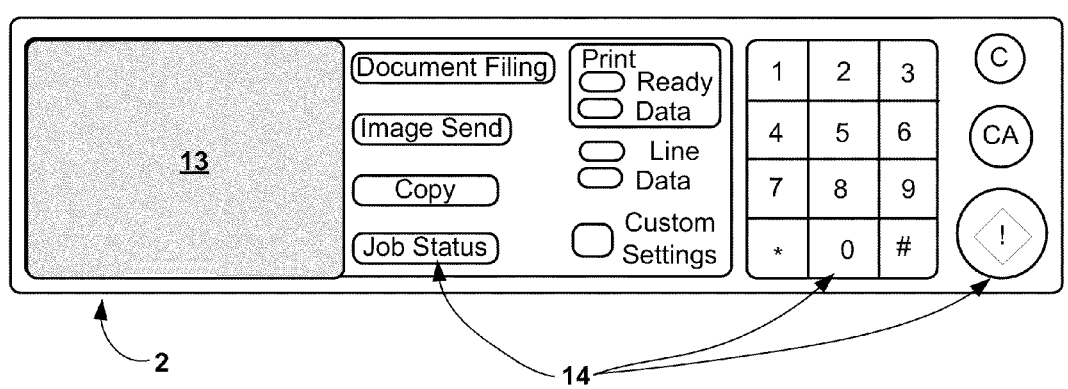
FIG. 2 is an image of an exemplary user interface for an imaging device.

Some embodiments of the present invention may be described with reference to FIGS. 1 & 2. These embodiments comprise an imaging device (IDev) 4 that may be a multi-function peripheral device (MFP) or a single function device. The imaging device 4 further comprises a user interface (UI) panel 2, which may comprise input buttons 14 and a display device 13 or may comprise a touch panel system with or without buttons 14. User input and display may also be performed through a separate UI device 8, which may be connected to the imaging device 4 by a communication link 12, such as a USB connection, a network cable, a wireless connection or some other communications link. UI device 8 may comprise an input device, such as a keyboard or buttons as well as a display device, which may also be a touch screen panel. UI device 8 may also comprise an interface for transfer of instructions that are input to the device 8 from a remote input device. This form of UI device 8 may comprise memory sticks, USB memory cards and other storage devices that may be configured to store input for transfer to an imaging device.

These embodiments further comprise a remote computing device (RCD) 6 that is linked to the imaging device 4 via a communications link 10, such as a network connection. This network connection may be a typical wired connection or a wireless link.

Embodiments of the present invention may provide menu data from the RCD 6 to the imaging device UI panel 2 or remote panel 8 via the network connection 10. Once this menu data is fed to the imaging device 4, an UI panel 2, 8 on the imaging device 4 may be used to interact with applications that run on the remote computing device 6. User input received from UI panels 2, 8 may be returned directly to the remote computing device 6.

A Web Service is a software application identified by a Uniform Resource Identifier (URI), whose interfaces and binding are capable of being defined, described and discovered by Extensible Markup Language (XML) artifacts and supports direct interactions with other software applications using XML based messages via Internet-based protocols.

An application on the remote computing device 6 may use one or more Web Services to control various features in the imaging device 4, such as enabling, disabling or setting device values or controlling device functions.

Embodiments of the present invention allow network applications running on remote computing devices to interact with the user of the imaging device through the imaging device 110 panel. These embodiments allow imaging device user interface (UI) control (i.e., touch panel, button/display) by applications. Some embodiments may also integrate custom display screens or menus with the native imaging device UI. Embodiments may hand off control of imaging device functions between standard operation modes performed on the imaging device in response to user input to an imaging device UI and open systems modes that utilize network resources, such as applications on RCDs, through user input at the imaging device UI.

Embodiments of the present invention comprise network-based applications that have full control over the imaging device UI to display text and graphics in any format. In these embodiments, the application can programmatically display buttons, textboxes, graphics, etc. in any layout desired.

In some embodiments, the UI layout is easy to program using a standard language, such as a markup language. These languages comprise Hypertext Markup Language (HTML), Extensible Markup Language (XML), Wireless Markup Language (WML), Extensible Hypertext Markup Language (XHTML) and other languages.

In some embodiments of the present invention a remote computing device application or server application is able to request a keyboard UI to be displayed on the imaging device display 12, 8. In some embodiments, this functionality is available on the imaging device and does not need to be recreated by remote computing device applications. In some embodiments, the remote computing device may define the keyboard prompt and default values. These embodiments may comprise a remote computing device that is able to rename imaging device UI buttons, such as the OK and Cancel buttons as well as define additional buttons.

In some embodiments, menu templates may be served to the imaging device UI by the imaging device itself 4 or from a remote computing device 6.

External Authorization Application

Some embodiments of the present invention may comprise a remote computing device application that is registered as the External Authorization server. The External Authorization application may control access to the imaging device and may have top-level control of the UI. UI control may be given to this application in the same manner that control is given to an internal auditor.

In these embodiments, when an imaging device system boots, it checks to see if an External Authorization application is registered. If so, the imaging device is placed in disabled mode and the application is contacted to take control of the UI. If the External Authorization server is not available, an error message may be displayed and the device may remain disabled. The imaging device may periodically try to contact the External Authorization server until it is available. Table 1 below describes what entity has control of the UI, in an exemplary embodiment, when the device is in a disabled state.

TABLE 1

UI Control in Disabled State

| Button Press | UI Control | Indicator Lights |
|---|---|---|
| Device boots | External Application | None |
| Document Filing | External Application | None |
| Image Send | External Application | None |
| Copy | External Application | None |
| Job Status | Device—standard Job Status screens | Job Status |
| Custom Settings | Device—standard Custom Settings screens | N/A |
| OS Mode | Not available when device is disabled | |

Remote Computing Device Applications

In embodiments of the present invention, access to the custom UI panels of imaging devices may vary from application to application. Some solutions, such as Document Management integration, may wish to leverage the native Image Send screens, but display some custom UI's to gather additional information about a scan job. Other solutions, like custom printing applications, may be accessed from a separate mode than the native functions.

In order to accommodate the diversified needs of these solutions applications, embodiments may support multiple integration points for UI control. These integration points are based on a user action ("trigger") for which applications may register. In some embodiments, applications may be registered with target devices so that the device knows that when "trigger A" occurs on the front panel to contact "remote computing device B" for instructions. In exemplary embodiments, applications may be integrated with an imaging device at any of several "trigger" points.

Remote computing devices may be registered to a specific function and contacted when that function's hardware key is pressed (e.g. Image Send) on the imaging device UI. Any UI information provided by the remote computing device may be displayed instead of the standard function screens native to the imaging device. This trigger may be used for applications that wish to replace the existing functions with completely custom UI's, such as an alternative scan solution or a specialized display, such as a "Section 508" compatible screen or other specialized-need interface that may have large buttons or other accommodations.

In some embodiments, each function on the imaging device may have a menu on the touch screen that remote computing devices, such as servers, can register. This enables solutions applications to provide custom content and still use some of the standard functionality provided by the imaging device. When a button assigned to a custom application is selected, a menu will be displayed with the solutions registered to that function. Users may select the desired solution and the remote computing device will be contacted for instructions.

In some embodiments, a stand-alone RCD mode that provides remote computing device application access can be accessed from the job queue portion of the UI that is displayed on every screen. This trigger point may be used for applications that do not fit within one of the standard device functions, such as custom printing solutions on an imaging device. When the RCD menu is selected, a menu will be displayed with the solutions applications registered to the generic RCD mode. Users will select the desired solution and the remote computing device will be contacted for instructions.

Hardware Key Interaction

In some embodiments of the present invention, when an imaging device is enabled, additional hardware keys may be used to manage the device. Hardware key assignments for an exemplary embodiment are shown in table 2.

TABLE 2

Exemplary Hardware Key Assignments

| Button Press | Standard IDev Mode | RCD Mode |
|---|---|---|
| Mode keys (Copy, Doc Filing, Image Send) and Custom Settings key | Clear current job settings, move to target screen | Clear current job settings, move to target screen |
| Job Status key | Move to Job Status, maintain current settings & UI location | Move to Job Status, maintain current settings & UI location |
| Clear (C) | Clears settings | Sends clear event to external application |
| Clear All (CA) | Clears settings, cancels job, and returns to default IDev screen | Cancels job and returns to default IDev screen (notification sent to external application) **When External Authorization is controlling the UI, only notification is sent |
| Start | Initiates scan function | Initiates scan function |
| Number keys | Input for copy count or fax numbers | Not used |
| * | Logs user out (disable device and contact External Authorization for screens) | Logs user out (disable device and contact External Authorization for screens) |

In some embodiments, in addition to the * key for logout, a timeout period may be implemented. Some embodiments also comprise an auto clear setting that can be configured for a given period of time, such as 10 to 240 seconds (or disabled). In these embodiments, when there is no activity for the time configured in auto clear, the device may automatically return to disabled mode and attempt to contact a remote computing device to retake control of the UI.

Error & Jam Notifications

Depending on a particular solution, a remote computing device application may have full or only partial control of the imaging device UI and a particular imaging job. In some embodiments, partial control may include cases where a remote computing device is monitoring clicks, but native modes are responsible for the UI interaction and controlling the job. Partial control may also include cases where the remote computing device application is integrated with a native mode (UI trigger=function custom menu). In these embodiments, the imaging device may handle all error and jam notifications with only a notification sent to the relevant remote computing device application.

For some embodiments, in cases where the remote computing device application has full control over the UI and the job, error and jam notifications may be handled differently depending on the type of error. For recoverable errors, a notification may be sent to the remote computing device application and the application may be responsible for displaying messages and resolving the error. For non-recoverable errors, the imaging device and RCD mode may interact to gracefully handle the error condition (e.g. provide user with instructions for clearing jam).

Control Handoffs

In some embodiments, at different points throughout an imaging job, several applications may need control over an imaging device including, but not limited to, an External Authorization application, a standard RCD application, an imaging device native mode and other applications. The following section describes, for an exemplary embodiment, the various steps in an exemplary job, the entities that may have control during each step, and what type of control may be allowed.

Step 1: User provides credentials to access the device at the device UI. This step may be controlled by a remote computing device, such as an External Authorization application or by Internal Accounting (native mode) in the imaging device itself. At the end of this step, the device is enabled. The External Authorization application may also specify default parameters or disable specific job parameters (e.g. default file format is PDF, but user may change; color mode is set to B/W and user may not change).

Step 2: User sets parameters for the job using one of the native imaging device modes or a standard RCD application. At the end of this step the user makes an input to initiate the job. When the input is made, an optional notification may be sent to the standard RCD application, which can then change job parameters if desired. An e-mail application is one example of an application that may request notification when the user input is made. A user may use native Image Send screens or other input to select scan options and choose e-mail recipients. A user may then select a custom application button and choose the scan-to-e-mail option from the menu. The e-mail application may then display custom screens for the user to set permissions for the file. Once a user places the original document(s) on the scanner and initiates the process, the e-mail application may capture the destination parameters set by the user and change the target destination to the e-mail application FTP server. The e-mail application may then receive the file, apply the appropriate permissions, and send to the e-mail recipients selected by the user. A remote computing device application may also want to retake control of the UI at this point, if, as in some embodiments, the application generates thumbnails of the scanned images and displays them to the user for verification.

Step 3: Once the job is initiated, the imaging device is responsible for scanning or RIPing the job and spooling it to the HDD. If the imaging device is configured to authorize jobs with an external authorization application, it may send a click report to the application and wait for instructions. The external authorization application may enable the job for sending/printing, cancel the job, or change job parameters (and then enable). As an example, a rules-based printing application may wish to change job parameters after it receives a click report. Some rules-based printing applications support rules-based printing and scanning that can limit what each user is allowed to do based on the time of day, the destination, or many other parameters. For example, only users in the marketing group may be able to scan high-quality color images. If a user from another group selects color and 600 dpi, a rules-based application may change the parameters to color and 200 dpi. At the end of this step the job should either be authorized or canceled.

Step 4: In some embodiments, this may be an optional step, where the standard RCD application in step 2 may have specified the destination as a HDD for temporary storage. This step may also be used, in some embodiments, by a Java application running on the imaging device. For example, a government office may have a custom encryption application running on the device that takes the scanned document, encrypts it, and then requests the imaging device to send it to the target destination selected by the user in step 2. In some embodiments, it may be beneficial to send a notification to the external authorization application after this step—because the imaging device does not know how long the file will be on the HDD or what the application is going to do with it—and after the send/print step.

Step 5: In the final step, the file is actually output. In typical embodiments, the file is either sent over the network or printed locally. At the end of this step, a notification that the job was successfully completed should be sent to the external authorization application and optionally, to the standard RCD application.

Device Control and Management API's

The API's may be used to allow a remote computing device application to control access to an imaging device for vend applications and to manage the device from a remote location.

Device Control and Vend API

In some embodiments of the present invention, a Device Control and Vend API allows applications to enable and disable access to the device and track click counts. The Device Control and Vend API may provide an RCD with the following controls:

Enable/disable device of function—this may allow an RCD to enable or disable access to the device as a whole or by function to enforce individual user privileges. In some exemplary embodiments, the functions listed in Table 3 may be selectively enabled or disabled by an application.

TABLE 3

Device Functions

| Enable/Disable | Description |
| --- | --- |
| Copy | Copy function (Copy button) |
| Image Send | Scan and fax function, plus send from Doc Filing (Image Send button) |
| Document Filing | All access to Document Filing functions (Document Filing button) |
| Print | Network prints, pull print from front panel, and print from Document Filing (No button control) |

Report clicks used—at the end of a successful job, the clicks used may be reported back to an RCD including:

TABLE 4

| Item | Job and Page Characteristics | | | | | | |
|---|---|---|---|---|---|---|---|
| | Copy | Print | Fax Send | PC-Fax | E-mail/FTP | Broadcast | Scan to HD |
| JOB Characteristics | | | | | | | |
| Job Mode | Yes | Yes | Yes | Yes | Yes | Yes | Yes |
| Broadcast Manage No. | No | No | Yes | Yes | Yes | Yes | No |
| User Name | Yes | Yes | Yes | Yes | Yes | Yes | Yes |
| Address | No | No | Yes | Yes | Yes | # | No |
| Start Time | Yes | Yes | Yes | Yes | Yes | Yes | Yes |
| End Time | Yes | Yes | Yes | Yes | Yes | Yes | Yes |
| Total Page | Yes | Yes | Yes | Yes | Yes | Yes | Yes |
| Result | Yes | Yes | Yes | Yes | Yes | Yes | Yes |
| Error Cause | No | No | Yes | Yes | Yes | Yes | No |
| Doc Filing | Yes | Yes | Yes | Yes | Yes | Yes | Yes |
| Save Mode | *1 | *1 | *1 | *1 | *1 | *1 | *1 |
| File Name | *1 | Yes | *1 | Yes | Yes | *1 | Yes |
| File Size | Yes | Yes | *1 | *1 | *1 | *1 | Yes |
| Resolution | Yes | Yes | Yes | Yes | Yes | Yes | Yes |
| Special | Yes | Yes | Yes | No | Yes | Yes | Yes |
| Finishing | Yes | Yes | No | No | No | No | No |
| File Format | No | No | No | No | Yes | Yes | No |
| Compression | No | No | No | No | Yes | Yes | No |
| PAGE Characteristics | | | | | | | |
| Copy | Yes | Yes | Yes | Yes | Yes | # | Yes |
| Paper Size | Yes | Yes | Yes | Yes | Yes | Yes | Yes |
| Simplex/duplex | Yes | Yes | Yes | Yes | Yes | Yes | Yes |
| Paper Type | Yes | Yes | Yes | Yes | No | No | Yes |
| Page | Yes | Yes | Yes | Yes | Yes | Yes | Yes |

*1—Yes when Document Filing is used

Debit mode—in these embodiments, when an application enables the device it may specify if the current job requires authorization. If so, the job will be spooled to memory and click information (e.g., as defined in Table 4) will be sent to an RCD. An RCD will then notify the device if the job should be deleted or output/sent. At this point, the application also has the option of changing job parameters. If the application does not require authorization, the job will continue as normal and a click report will be sent at the end of the job.

Print job accounting—in these embodiments, an RCD may wish to monitor print jobs along with walk-up functions. For print job accounting, an IDev may monitor all incoming print jobs and send accounting data in the PJL header to an RCD for verification before printing the job. The RCD will evaluate the accounting data (or lack thereof) and inform the IDev to continue with or cancel the job.

Report on unidentified jobs—in these embodiments, an RCD may also wish to monitor print jobs that it cannot associate to a specific user, such as device reports and incoming fax jobs. The RCD can register to receive click counts for all unidentified jobs, so that it may bill them to a general account.

Device Management API

In some embodiments of the present invention, a Device Management API allows a network application to remotely setup and manage the imaging device. In exemplary embodiments, the Device Management API may provide an RCD with the following controls:

Device status—an RCD may request the current status of the device. This is the same status information as reported on the embedded web pages.

Device configuration—an RCD can retrieve a list of installed options supported by the device.

Web Page settings—an RCD application can retrieve and set any of the values that are configurable on the embedded web pages.

Key Operator Programs—an RCD application can retrieve and set any of the values that are configurable in Key Operator Programs, including software keys.

Custom Settings—an RCD application can retrieve and set any of the values that are configurable in Custom Settings.

Job Status—an RCD application can retrieve the current job queue and history information and reprioritize or delete jobs in the queue.

Click counts—an RCD application can retrieve device total counts and clicks for each function by account code.

Data Security settings—an RCD application may retrieve the status information on the DSK (e.g. last erase) and initiate data clear functions.

RED data—an RCD can retrieve all data typically sent in a RED message.

Remote reboot—an RCD can initiate a reboot of the imaging device.

The above groupings are provided only as an exemplary embodiment detailing which settings should be included. In some embodiments, actual API's should be grouped by functional areas since there may be overlap between Key Operator settings and web page settings.

Internal Accounting API

In some embodiments, an Internal Accounting API may allow a remote computing device application to configure internal accounting and report click counts. In some exemplary embodiments an Internal Accounting API may include:

Set Auditing Options—an RCD may set auditing options including which modes auditing is enabled for, "account number security", and "cancel jobs of invalid accounts."

Manage Account Codes—an RCD can add, edit, or delete account codes

Account Limits—an RCD application can specify a maximum number of clicks by function for individual account codes or for all account codes Account Reset—an RCD application can reset the click count for an individual account or for all accounts Retrieve Clicks—an RCD can retrieve the number of clicks by function for each account code Font and Form Management API Some embodiments of the present invention may comprise a Font and Form Management API, which allows an RCD application to remotely download and manage fonts and forms in mass-storage. In some exemplary embodiments, a Font and Form Management API may provide a remote computing device with the following controls:

Mass storage control—an RCD application can retrieve mass storage status information including storage capacity, space available, and write-protect mode plus modify write-protect status.

Resource list—an RCD application can retrieve a list of stored fonts and forms including font or macro ID, font number, font/form name, escape sequence, and file size.

Download resource—an RCD application can download PCL fonts, PCL macros, and PS fonts and forms. Any special processing that is performed when a resource is downloaded via the web pages will also be performed when the resource is downloaded via Open Systems.

Delete resource—an RCD application can delete any resource stored in mass storage.

Upload resources—an RCD application can upload an individual or all resources. On devices where effective memory management is unavailable, a server application can use this function to "defrag" mass storage.

Font/macro ID's—an RCD application can assign or modify the ID's assigned to PCL fonts and macros.

Firmware Management API

In some embodiments of the present invention, a Firmware Management API may allow a remote computing device or network application to remotely download and manage the imaging device firmware. In some exemplary embodiments, a Firmware Management API may provide a remote computing device (e.g., a server) with the following controls:

Firmware versions—an RCD application can retrieve the current firmware version numbers.

Service mode—an RCD application can place the MFP in service mode to lockout other jobs that will interfere with firmware upgrade. Upon receiving a service mode request, the IDev will stop accepting incoming jobs, complete all jobs in the queue, and then notify the server that it is in service mode.

Update firmware—an RCD can download an updated firmware version to the device. If a reboot is necessary, the IDev will perform it automatically when download is complete.

Download status—the IDev will send a status notification (success/error) to an RCD after firmware download.

Revert to previous version—if firmware update is not successful, the application can request the IDev to revert to the previous firmware version.

Device Function API's

In some embodiments of the present invention, device function API's allow a remote computing device application to use existing imaging device functionality to provide new custom solutions.

Image Send API

In some embodiments, an Image Send API may provide the remote computing device application with the following controls:

Image Send Parameters—a remote computing device application can get and set values for the following scan and fax parameters:
COLOR OR B/W
IMAGE MODE—TEXT, TEXT/PHOTO, PHOTO; EXPOSURE LEVEL
RESOLUTION
FILE FORMAT—FILE TYPE, COMPRESSION, AND PAGES PER FILE
ORIGINAL—ORIGINAL SIZE, SIMPLEX/DUPLEX, ROTATE, AND JOB BUILD
FILENAME
SUBJECT
MESSAGE
SENDER
SCHEDULE SEND TIME
PAGE DIVISION (BOOK SCANNING)
COVER PAGE
TRANSMISSION MESSAGE (CONFIDENTIAL, URGENT, ETC.)
THIN PAPER SCANNING
DESTINATION
DOCUMENT FILING Initiate Scan—the remote computing device application can initiate the scan function (same as user pressing start button).

In some embodiments, a remote computing device can change the default values on the imaging device or the values for the current job. For the current job, the remote computing device may also specify if scan parameters may be modified by the user or not. If one remote computing device application (e.g. Access Control) specifies that a parameter cannot be changed and then a second application (e.g. Document Management) tries to set the parameter, a notification may be sent to the second application and the setting will not be changed.

Print API

In some embodiments, print jobs may be submitted by remote computing device applications using standard printing channels. In some exemplary embodiments, a Print API may provide a remote computing device with the following additional control:

PJL sniffing—an RCD application can register with the IDev to be contacted for instructions when a specific PJL command is found in a print job. The RCD can then instruct the IDev to replace the command, cancel the job, or continue printing. This interface may be used in applications like accounting and other-brand compatibility.

Copy API

In some embodiments of the present invention, a Copy API may provide a remote computing device with the following exemplary controls:

Copy Parameters—an RCD application can get and set values for the following copy parameters:
COLOR OR B/W
EXPOSURE—TEXT, TEXT/PHOTO, PHOTO, SUPER PHOTO; EXPOSURE LEVEL
PAPER SELECT (BY TRAY)
COPY RATIO
2-SIDED COPY—1To1, 1To2, 2To2, 2To1; BINDING EDGE
OUTPUT—OUTPUT TRAY, SORT, STAPLE, GROUP, OFFSET
ORIGINAL SIZE
SPECIAL FUNCTIONS—MARGIN SHIFT, ERASE, PAMPHLET, ETC.
DOCUMENT FILING Initiate Copy—an RCD application can initiate the copy function (same as user pressing start button).

In some embodiments, a remote computing device can change the default values on the imaging device or the values for the current job. For the current job, the remote computing device may also specify if copy parameters may be modified by the user or not.

Document Filing API

In some embodiments of the present invention, a Document Filing API may provide a remote computing device with the following exemplary controls:

Backup/restore—the remote computing device application can import and export a batch file with all Document Filing data. In some embodiments, this package will be in a proprietary format since it contains documents that are password-protected and should not be accessed individually—this is typically for restore in case of failure or cloning to other devices.

File/folder list—the remote computing device application can retrieve, modify, and create new files and folders to be stored on the IDev (also covered in device management).

Download file—the remote computing device can download a new file to the Document Filing systems and specify folder, filename, username, and password.

User list—the remote computing device application can retrieve, modify, and create new users to be stored on the IDev (also covered in device management).

HDD Status—the remote computing device application can retrieve the current HDD status including the % allocated to the main folder, quick folder, and custom folders and the % remaining.

Filing Parameters—the remote computing device application can get and set values for storing a file to Doc Filing including:
EXPOSURE
RESOLUTION
ORIGINAL—SIZE, SIMPLEX/DUPLEX
FILE INFORMATION—USERNAME, FILENAME, FOLDER, CONFIDENTIAL, PASSWORD
SPECIAL MODES—ERASE, DUAL PAGE COPY, 2IN1, JOB BUILD, CARD SHOT Initiate Print—the remote computing device application can select a stored file and initiate a print including the following parameters:
PAPER SIZE/SOURCE
OUTPUT—SORT/GROUP, OUTPUT TRAY, STAPLE, PUNCH, OFFSET
SIMPLEX/DUPLEX (TABLET/BOOKLET)
TANDEM PRINT
NUMBER OF COPIES
DELETE OR STORE AFTER PRINTING Initiate Send—the remote computing device application can select a stored file and initiate a send including the following parameters:
RESOLUTION
FILE FORMAT
DESTINATION
TIMER
SENDER
FILENAME
SUBJECT
MESSAGE Security Allowing external applications to control an imaging device opens up the imaging device to new security vulnerabilities. In embodiments of the present invention that provide some security measures, the following exemplary items are security concerns that may be addressed by the remote computing device interface.

Access to remote computing device interfaces may be limited to valid applications. Embodiments provide extensive access and control of the imaging device, which poses a significant security risk. The interface of these embodiments may be protected from access by attackers, while maintaining ease of setup and use for valid solutions.

Confidential data (user credentials and job data) may be protected during network transfer. User credentials and job data may be secured during network transfer to ensure that it cannot be stolen, an intruder cannot monitor device activity, and a man-in-the-middle attack cannot change messages. Imaging devices may support Secure Sockets Layer (SSL) and other connections to ensure data is safe while being communicated between the imaging device and remote computing device applications.

Administrators may have the ability to lock-down imaging device access. For users with strict security policies, administrators may have the ability to disable access by remote computing devices or limit access to specific applications. Administrators may have an option to register the limited applications that they wish to access the imaging device interfaces.

Remote computing device applications may ensure the imaging device is not being "spoofed." The remote computing device may be able to authenticate an imaging device that it is contract with it to ensure an intruder cannot imitate the imaging device to collect network configuration and password information, monitor file/folder structures of a document management system, or spoof security settings and DSK status of the imaging device.

A remote computing device may ensure that the server is not being "spoofed." The imaging device must be able to authenticate all remote computing devices that it is in contact with to ensure that an intruder is not spoofing the remote computing device's IP address. By pretending to be the remote computing device, an intruder could steal user credentials, redirect scanned documents, change device settings or firmware, or bring down the access control system (either to provide access to unauthorized users or initiate a denial of service attack for valid users).

Access control/vend applications may not be compromised when a remote computing device is unavailable. When the remote computing device is unavailable, it may not be acceptable to provide open access to the device. If the remote computing device is unavailable at startup or becomes unavailable at anytime (e.g. someone disconnects network cable), the imaging device may immediately be disabled and an error message displayed.

An administrator may be able to adjust a security level based on company and application requirements. Security requirements can have a large impact on the time it takes to develop a remote computing device application and the resources required to implement the solution. Users using some embodiments may range from a small business with one imaging device, no IT staff, and a simple scan or print application to a large government office using access control and audit trails to track all device activity. The security measures used to protect imaging device interfaces may be adjustable by the administrator to match the target environment.

The imaging device and remote computing device applications may be able to hand-off user credentials. Users may be prompted to login at multiple points throughout a job. For example, an access control application or accounting application may control total device access, the imaging device may have user authentication enabled for Image Send, and a document management application may require user login before showing a folder list. In many environments, all of these applications will use a common user database. In some embodiments, it is, therefore, desirable for the applications to pass user credentials to each other, so that each one does not have to repeat the authentication process.

Some embodiments of the present invention may be described with reference to FIG. 3. These embodiments comprise an imaging device only, which is configured to interact with a remote computing device, such as a server through a communications link. The imaging device 30 comprises a user interface 32, which comprises a user input device 34, such as a keypad, one or more buttons, knobs or switches or a touch-screen panel and a display 36, which may comprise user input device 34 in the form of a touch-screen panel.

Imaging device 30 will typically be capable of performing one or more imaging functions including, but not limited to, scanning, printing, copying, facsimile transmission (sending and receiving) and others.

Figure 3:
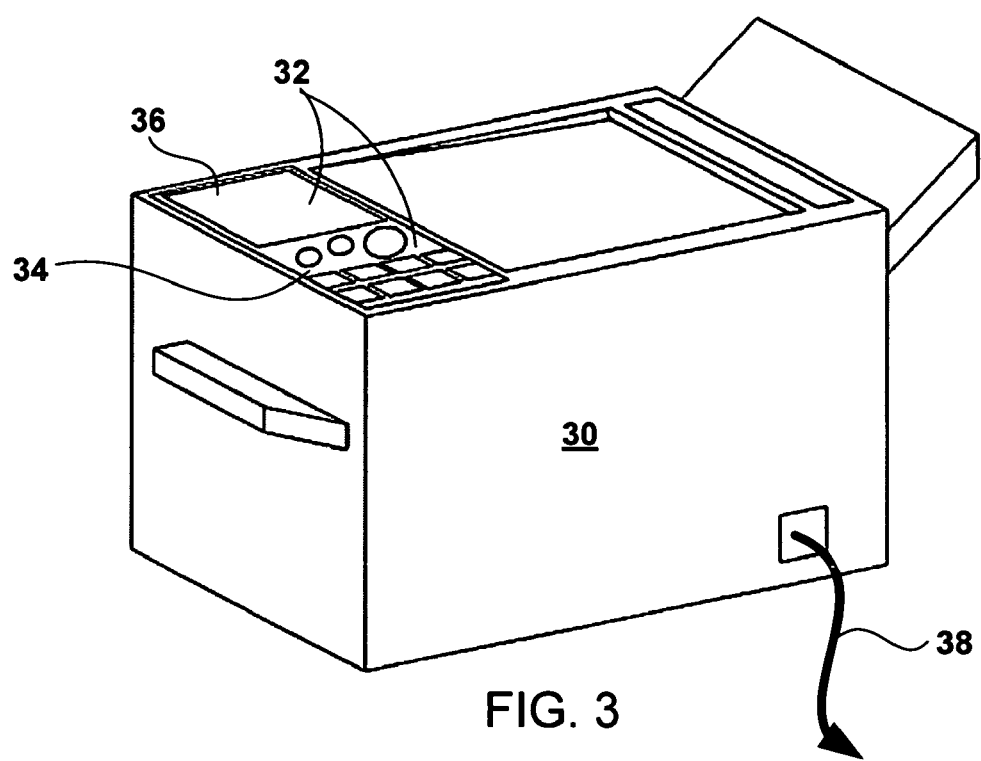
FIG. 3 shows an exemplary imaging device.

These embodiments further comprise a communications link 38, which may be a wired connection (as shown in FIG. 3) comprising a network cable, a Universal Serial Bus (USB) cable, a serial cable, a parallel cable, a power line communication connection such as a HomePlug connection or other wired connections. Alternatively, the communications link 38 may comprise a wireless connection, such as an IEEE 802.11

(b) compliant connection, a Bluetooth connection, an Infrared Data Association (IrDA) connection or some other wireless connection.

Figure 4:
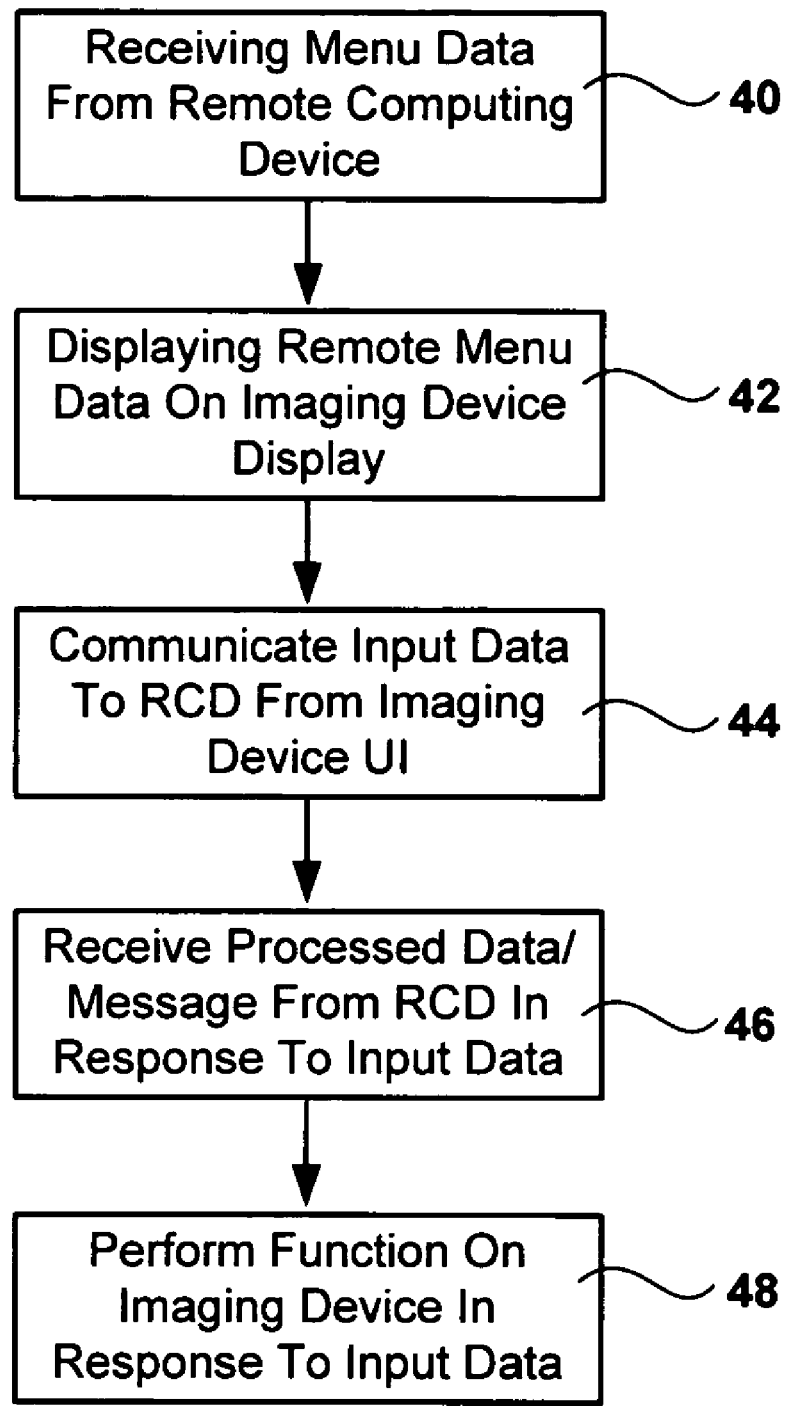
FIG. 4 is a chart depicting steps of an imaging device method.

The operation of some imaging device embodiments may be explained with reference to FIG. 4. In these embodiments, menu data is received 40 from a remote computing device (not shown in FIG. 3), which is connected to the imaging device 30 via the communication link 38 through a wired or wireless connection. This menu data is then displayed 42 on the imaging device user interface display 36. This display of remote menu data is intended to prompt a user to make an input on the user interface input device 34.

Imaging devices of these embodiments are further configured to accept input from a user in response to a display of remote menu data and communicate 44 that user input to a remote computing device. In some embodiments, this user input data will be processed by a remote computing device. This may comprise running an application on the remote computing device. This processing may also comprise accessing and communicating data that is stored on the remote computing device.

The imaging devices of these embodiments are further configured to receive 46 data resulting from processing the user input data. This may comprise data generated by an application running on the remote computing device in response to the user input. The imaging device may also receive data that was stored on a remote computing device, such as a file server, in response to processing the user input.

Once the imaging device 30 has received 46 the processed data, the imaging device 30 may perform 48 a native function in response to the data or using the data. For example, and not be way of limitation, the imaging device 30 may print a document that was stored on the remote computing device and modified on the remote computing device according to the user input. As another non-limiting example, the imaging device 30 may active or enable functions (i.e., scanning, copying, printing, fax transmission) on the imaging device in response to the receipt 46 of processed data.

Figure 5:
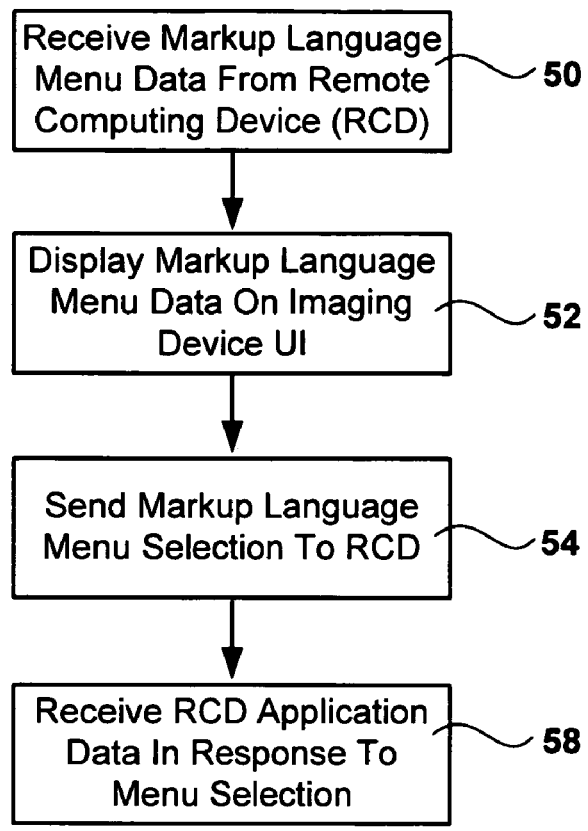
FIG. 5 is a chart depicting steps of an imaging device method using a markup language.

Some, more specific, imaging device embodiments may be explained with reference to FIG. 5. In these embodiments, the imaging device 30 is configured to receive 50 menu data formatted in a markup language from a remote computing device. The communication link by which the menu data is communicated may be established and maintained using a Hypertext Transfer Protocol (HTTP). The markup language may comprise terms from Hypertext Markup Language (HTML), Extensible Markup Language (XML), Wireless Markup Language (WML), Extensible Hypertext Markup Language (XHTML) and/or other languages.

Once the menu data is received 50, it may be displayed 52 on the imaging device user interface display 36. As in previously described embodiments, the menu data is typically intended to prompt user input on imaging device user interface 32. Display 52 of the remotely-stored menu data may be accomplished with a browser application that is native to the imaging device 30.

In these embodiments, the imaging device 30 is further configured to route 54 user input received though its user interface 32 to a remote computing device. The remote computing device that receives the user input may then run an application or otherwise process the user input and return the results of the processing to the imaging device 30. Accordingly, the imaging device 30 is further configured to receive 58 processed data from a remote computing device. In some embodiments, the imaging device 30 may perform one or more functions in response to the receipt 58 of processed data.

Figure 6:
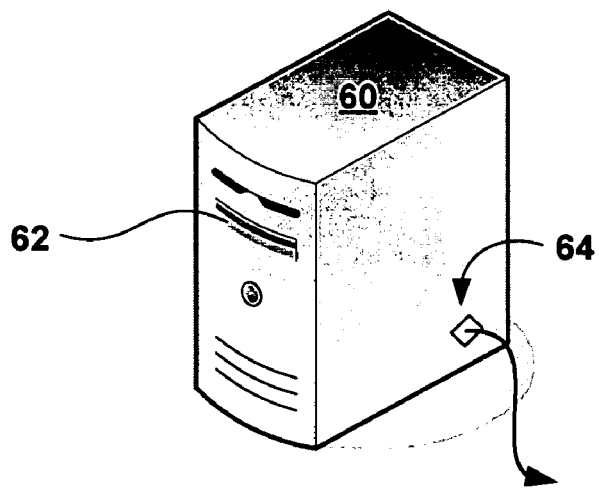
FIG. 6 shows an exemplary remote computing device embodiment.

Some embodiments of the present invention may be explained with reference to FIG. 6. These embodiments comprise a remote computing device (RCD) 60, which has a communications link 64. Communications link 64 may be a wired connection (as shown in FIG. 6) comprising a network cable, a Universal Serial Bus (USB) cable, a serial cable, a parallel cable, a powerline communication connection such as a HomePlug connection or other wired connections. Alternatively, the communications link 64 may comprise a wireless connection, such as an IEEE 802.11(b) compliant connection, a Bluetooth connection, an Infrared connection, such as those defined in the Infrared Data Association (IrDA) standard or some other wireless connection. In some embodiments, RCD 60 may further comprise a data storage device 62, which is typically a hard drive, but may also be an optical drive device, such as an array of compact disk drives, flash memory or some other storage device.

Figure 7:
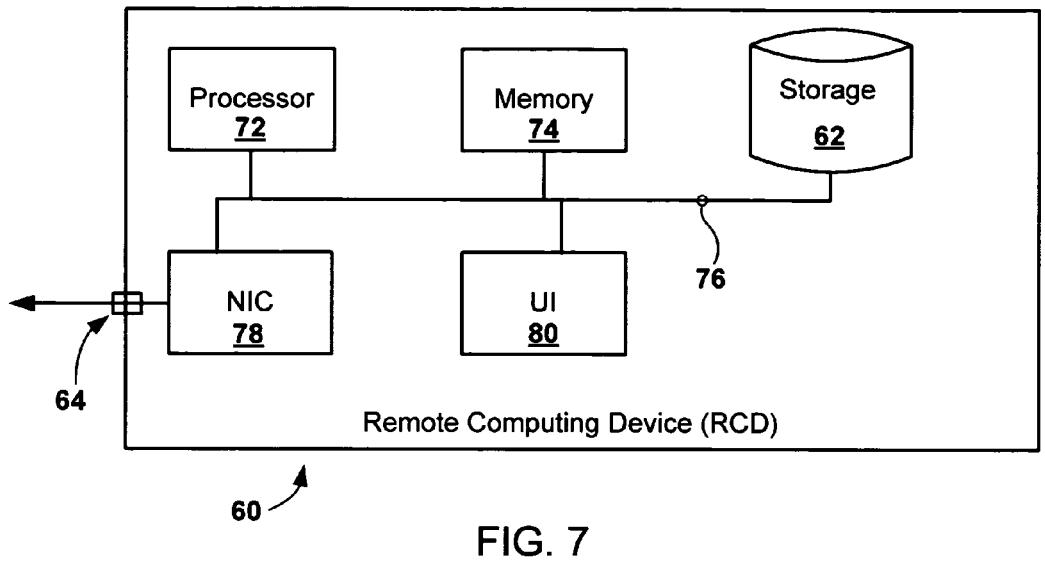
FIG. 7 is a diagram showing components of an exemplary remote computing device.

Embodiments of RCD 60 may be further described with reference to FIG. 7. In these embodiments, RCD 60 comprises a processor 72 for processing data and running programs such as operating systems and applications. RCD 60 may further comprise memory 74, which may be in the form of Random Access Memory (RAM) and Read Only Memory (ROM). Generally, any applications processed by processor 72 will be loaded into memory 74. RCD 60 may further comprise a network interface 78, which allows RCD 60 to communicate with other devices, such as an imaging device 30. In some embodiments, RCD 60 may also comprise a user interface 80, but this is not required in many embodiments. Storage 62 may be used to store applications and data that may be accessed by an imaging device 30 of embodiments of the present invention. Processor 72, memory 74, storage 62, network interface 78 and, optionally, user interface 80 are typically linked by a system bus 76 to enable data transfer between each component. Communications link 64 may couple the RCD 60 to other devices via network interface 78.

Figure 8:
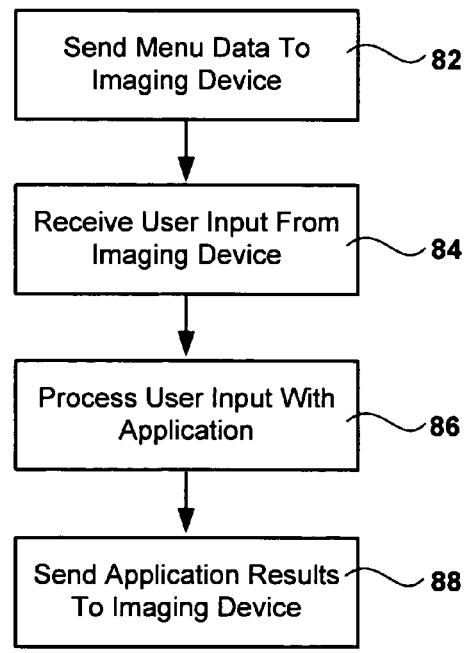
FIG. 8 is a chart showing steps of a remote computing device method.

In some embodiments, described with reference to FIG. 8, an RCD 60 may comprise menu data stored on storage device 62 or in memory 74. This menu data may be configured for display on an imaging device user interface 32. Menu data may be stored in many formats and configurations. In some embodiments menu data may take the form of terms expressed with a markup language. The markup language may comprise terms from Hypertext Markup Language (HTML), Extensible Markup Language (XML), Wireless Markup Language (WML), Extensible Hypertext Markup Language (XHTML) and/or other languages. In these embodiments, menu data may be sent 82 through a communications link 64 to an imaging device 30. Accordingly, menu data configured for display on an imaging device is stored on RCD 60.

An RCD 60, of some embodiments, will be further configured to receive 84 user input obtained through the user interface 32 of an imaging device 30 and transferred to the RCD 60 over communications links 38 & 64. Once this input data is received at an RCD 60, the input data may be processed 86. This processing 86 may comprise conversion of the data to a new format, execution of commands contained within the data or some other process. Once the input data has been processed 86, the processed output may be sent 88 back to the imaging device 30 where the processed output may be used in an imaging device process or function.

Figure 9:
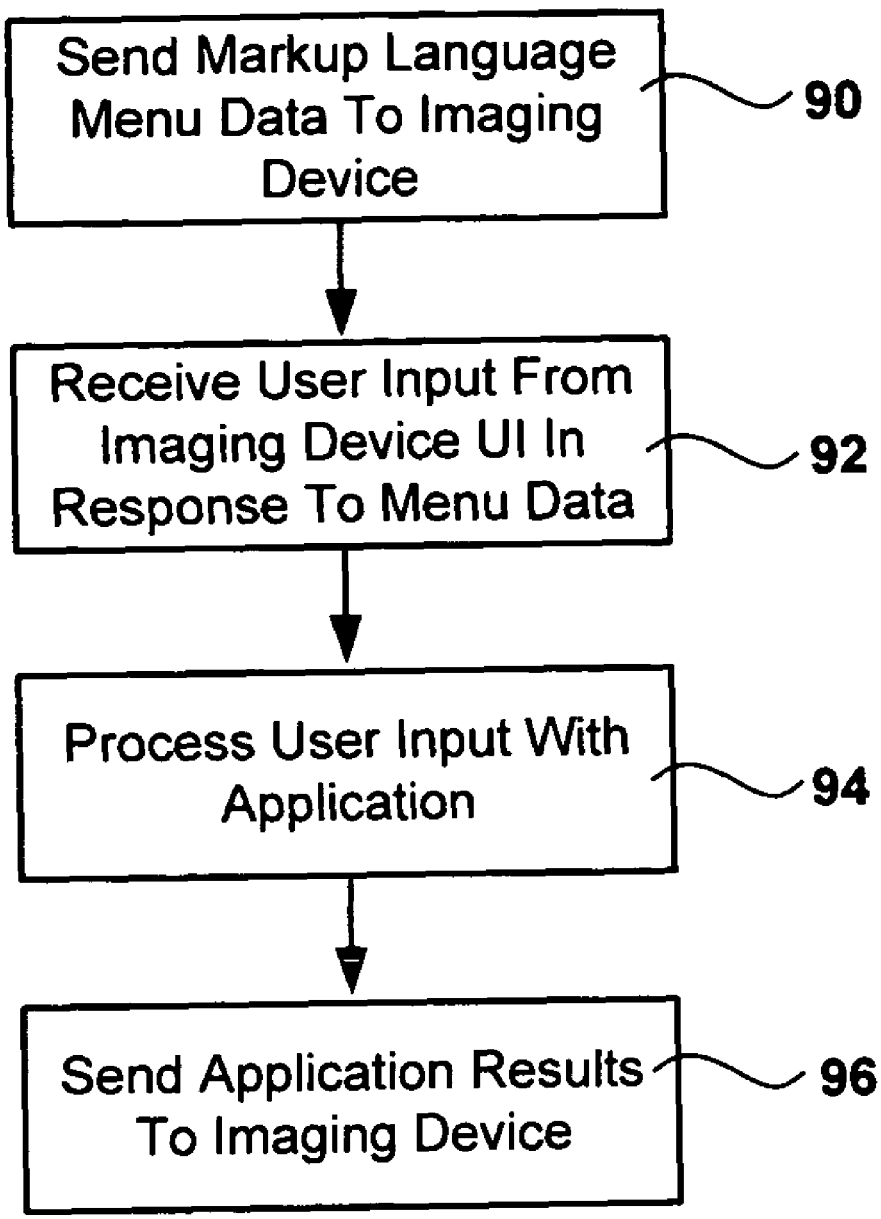
FIG. 9 is a chart showing steps of a remote computing device method using a markup language.

In some embodiments, as described with reference to FIG. 9, an RCD 60 may send 90 menu data configured for an imaging device display 36 using a markup language. The markup language menu data is then received at the imaging device 30 and displayed to a user. Typically, this will prompt the user to enter an input on the imaging device user interface 32. This user input will then be sent by the imaging device 30 to the RCD 60. The RCD 60 will then receive 92 the input data prompted by the display of the menu data on the imaging device 30. Once received, the input data may be processed 94 on the RCD 60. Processing may comprise the selection, recordation and/or modification of a form, document or other data stored on RCD 60, the authorization of a user identified by the user input, the translation of a document input by the user, generation of a map or other directions related to user input or some other process or function. After this processing, the RCD 60 may send 96 the results of the processing to the imaging device 30.

Figure 10:
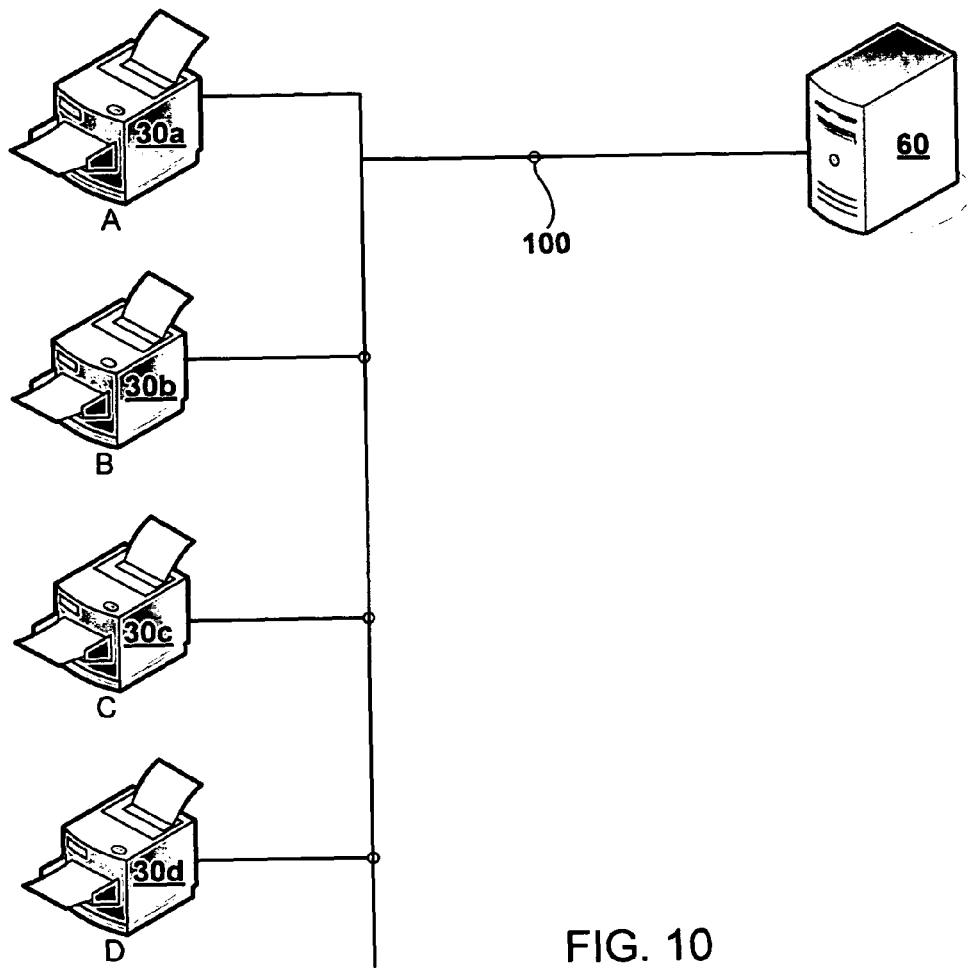
FIG. 10 is a diagram showing a system comprising multiple imaging devices in connection with a remote computing device.
Figure 11:
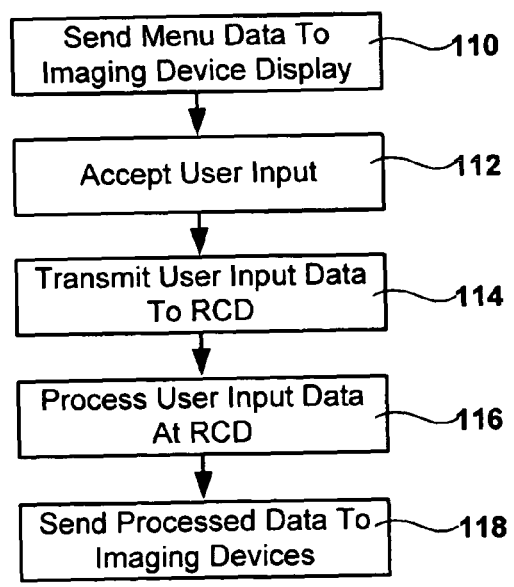
FIG. 11 is a chart showing steps of a method comprising RCD processing of user input data.

Some embodiments of the present invention may be described with reference to FIGS. 10 & 11. These embodiments comprise at least one RCD 60 and a plurality of imaging devices 30a-30d. In these embodiments, at least one of the imaging devices 30a-30d comprises a user interface 32 with a display 36 and user input panel 34 that is integral with the display (i.e., touch-screen) or a separate input unit. RCD 60 is connected to imaging devices 30a-30d by a communications link and network 100 to enable data transmission between RCD 60 and imaging devices 30a-30d.

In these embodiments, menu data is stored on RCD 60 and sent 110 to at least one of the imaging devices 30a-30d where the menu data is displayed on a user interface. Any of Imaging devices 30a-30d that receive the menu data are configured to accept 112 and transmit 114 user input to an RCD 60. Once the user input data is received at the RCD, the data may be processed 116 as discussed in previously described embodiments. The result of processing 116 may then be sent 118 back to any combination of the imaging devices 30a-30d.

In these embodiments, a single RCD 60 may be used to provide processing power, resources and functionality to a plurality of imaging devices 30a-30d without reproducing these resources in each imaging device. In some embodiments, data generated by input on one imaging device 30a may be directed to another imaging device 30d for processed data output or final processing.

Figure 12:
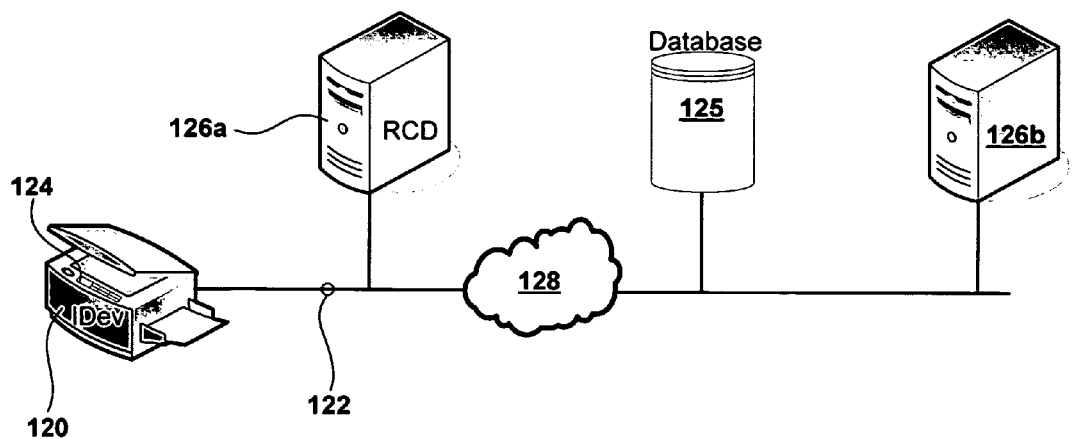
FIG. 12 is a diagram showing components of some embodiments comprising linked resources.

Some embodiments of the present invention may be described with reference to FIG. 12. In these embodiments, an imaging device (IDev) 120 comprises a user interface 124, which is capable of receiving user input and displaying data to a user. The user interface 124 will typically comprise a display, often in the form of a touch panel. The display may be used to display data to a user. This data may comprise menu data to prompt for a user selection or data entry, such as a user ID and password, form selection or some other input. The imaging device 120 has a communication link 122, which may comprise a typical computer network connection, a serial cable or some other wired or wireless communication link as described in other embodiments. The communication link 122 may connect the imaging device 120 to a remote computing device (RCD) 126a, 126b, such as a server. The RCD 126a, 126b may be used to store documents, such as forms, and other data and make that data accessible from the imaging device 120. The RCD 126a, 126b may also execute applications that interact with or receive input from the imaging device 120 and its user interface 124. In some embodiments, a database 125 may be linked to the imaging device 120 and/or an RCD 126a, 126b. In some embodiments, an RCD 126b or database 125 may be connected to an IDev 120 over a wide area network such as the internet 128.

Accounting Data Maintenance Embodiments

Some embodiments of the present invention comprise methods and systems for maintaining imaging device (IDev) accounting data when a primary server becomes unavailable. These embodiments comprise a lightweight accounting backup server (LABS) application capable of running on other servers or practically any networked computing device.

In a typical imaging device system, IDevs are placed under accounting control, meaning that they are connected to an application running on a server that is tasked with recording the device's activity. In addition to recording device activity, such as the number of copies made by each individual or on each account, a server application may also enable and disable IDev functions in relation to a user's credentials. This is done for the purpose of being able to charge accounts or individuals for the use of the IDev. In a typical system, when an accounting application fails or becomes temporarily unavailable, the IDev may be entirely disabled, preventing users from using the IDev to accomplish their tasks. The IDev may also remain enabled but with no record of the IDev usage. Both of these alternatives are unacceptable in a typical commercial setting.

Embodiments of the present invention comprise methods and systems that have the capability to continue providing accounting control over an imaging device when the main accounting server is down. In these embodiments, this is achieved with a lightweight accounting backup server (LABS) running on one or more personal computers in the system. When the primary accounting server returns to service, it may query the LABS for their accounting data and then update the primary IDev activity log.

Some embodiments of the present invention may comprise devices with a list of lightweight accounting back-up servers (LABS) that are available to that device. This information may be in the form of a uniform resource locator (URL) pointing to the LABS application's web server entry points. This list can be managed manually or can be populated by some form of discovery mechanism. When the primary server becomes disabled the IDev may attempt to connect to the first LABS on the list and may subsequently continue to connect to each consecutive LABS on the list until it succeeds. Once this occurs, the LABS may take over the accounting control of the IDev.

In some embodiments, the LABS may not fully implement the same set of features that the primary accounting server (PAS) application implements. For example, and not by way of limitation, the LABS may comprise only departmental information for specific departments that typically use a particular IDev rather than have whole enterprise data as in the primary accounting server (PAS). A LABS may implement all the function of a PAS, or it may implement a limited subset. In some embodiments, the LABS may only implement user login and click count functions. In these embodiments, some IDev functions may be unavailable to a user.

When the primary accounting server comes back online a message may be sent to the IDev indicating that the PAS is back in service. The IDev may then notify any LABS and instruct them to transfer any temporary IDev accounting log (TIAL) data they have recorded to the primary server. Finally, the IDev may return to sending accounting data to the primary accounting server until such time as the primary server becomes unavailable again.

In some embodiments, the PAS may communicate directly with a LABS when requesting TIAL data and when receiving TIAL data from the LABS. However, in some embodiments, direct LABS to PAS communication may not be used and communication may be routed through the IDev.

Some embodiments of the present invention may comprise an imaging device (IDev) in communication with one or more additional IDevs and one or more remote computing devices (RCDs) running LABS applications. These IDevs may also have communication with a primary accounting server.

Figure 13A:
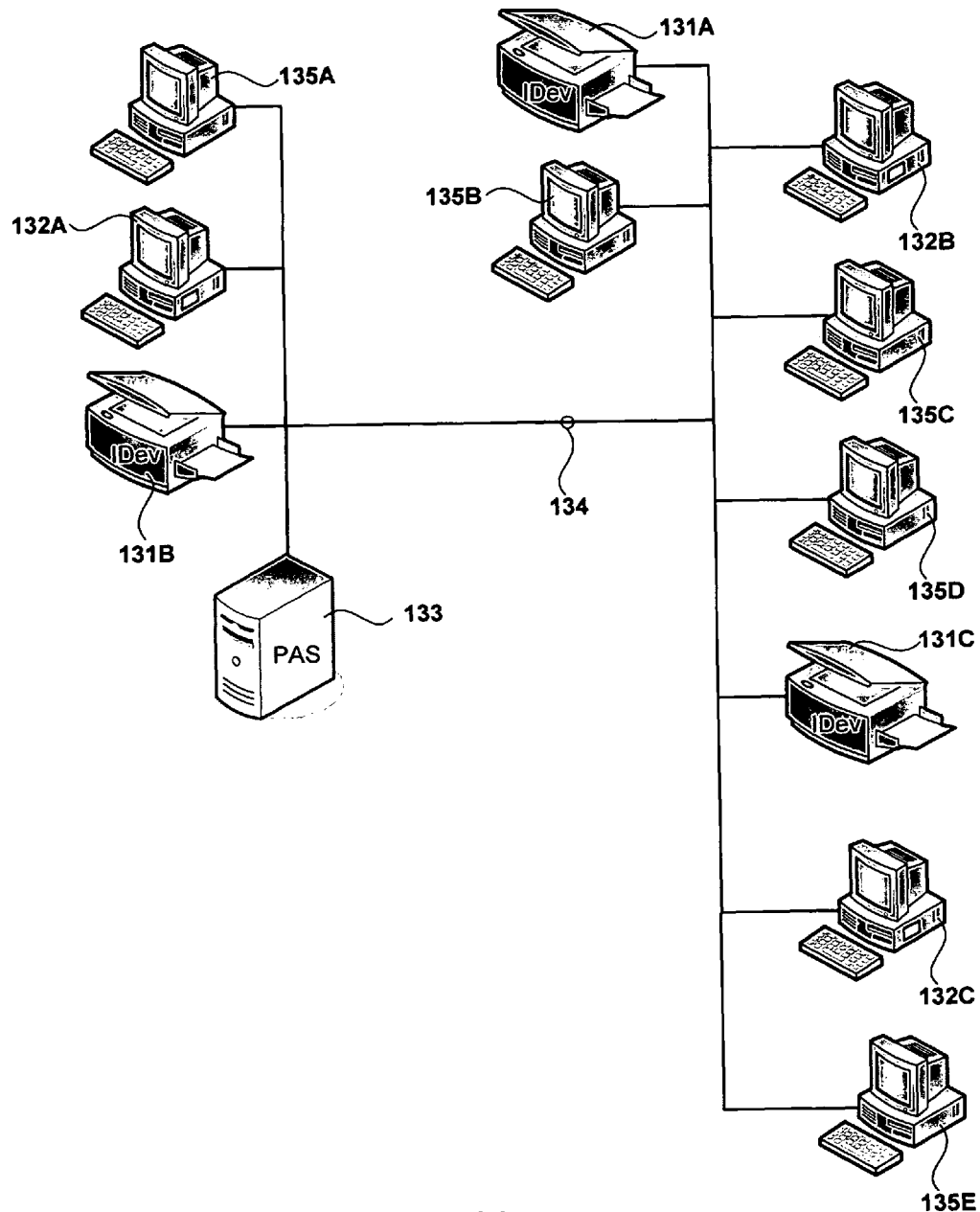
FIG. 13A is a diagram showing an exemplary system comprising IDevs, computing devices, a primary accounting server, and LABSs.

Some embodiments of the present invention may be described with reference to FIG. 13A. These embodiments may comprise one or more networked computing devices 135A-135E & 132A-132C which are linked with one or more accounting-controlled Imaging Devices (IDev) 131A-131C through a communication network 134. These IDevs 131A-131C and computing devices 135A-135E & 132A-132C may also be linked with a Primary Accounting Server (PAS) 133. The PAS may store IDev activity data and accounting data received from the IDevs 131A-131C.

Some of the networked computing devices 135A-135E & 132A-132C on the network 134 also function as LABS 132A-132C. These LABS 132A-132C are applications running on computing devices that provide some kind of accounting control and/or IDev activity recording functions. An LABS 132A-132C may be part of a computing device that has some other primary function. In some embodiments, a 132A-132C may be part of a typical client computing device or workstation that is used for word processing, drafting or some other primary application. The LABS application may run in the background and be transparent to a primary computing device user. 132A-132C.

In the event that the primary accounting server (PAS) 133 goes offline, the IDevs 131A-131C may send their accounting data to the lightweight accounting backup servers (LABS) 132A-132C which may temporarily store the data until the primary accounting server (PAS) 133 comes back online.

Figure 13B:
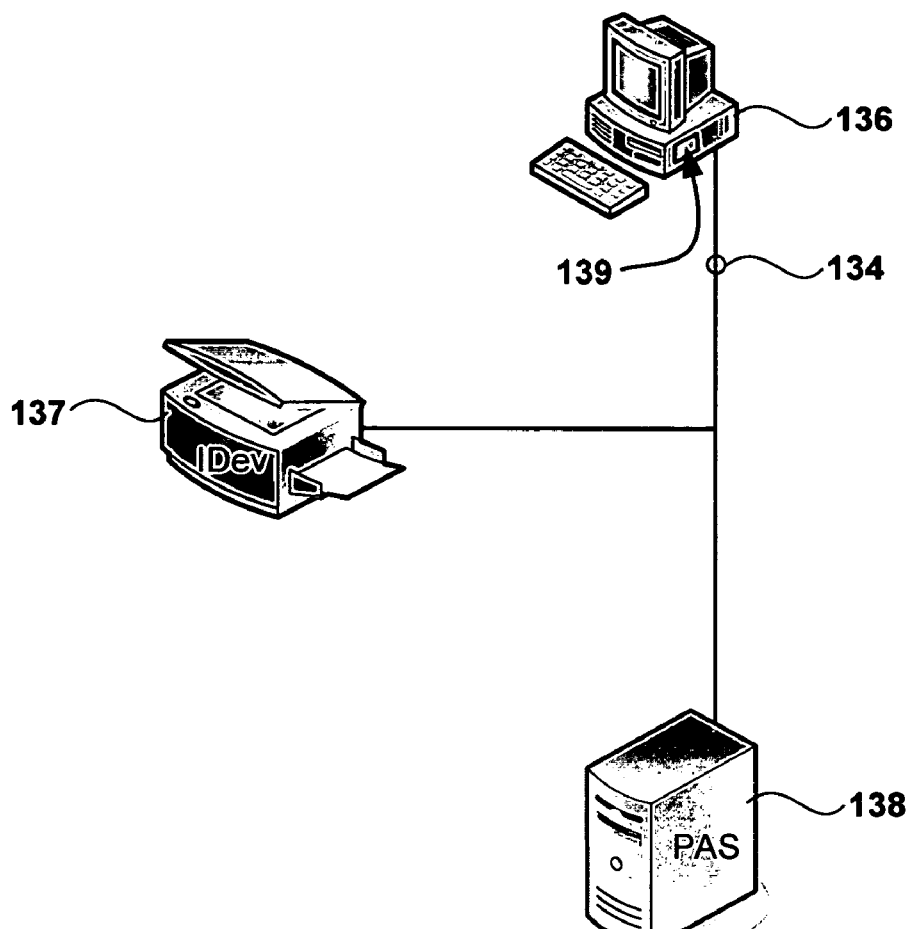
FIG. 13B is a diagram showing an exemplary system comprising an IDev, a computing device comprising a LABS and a primary accounting server.

Some embodiments of the present invention may also be described with reference to FIG. 13B. In these embodiments, a system may comprise a computing device 136 in communication with an imaging device (IDev) 137 and a primary accounting server 138. In these embodiments, the computing device comprises a component that functions as a lightweight accounting back-up server (LABS) 139. The components may be connected with a network 134, such as a wired or a wireless network. The components of these embodiments function as in other embodiments, but the scale of the network is much smaller.

Figure 14A:
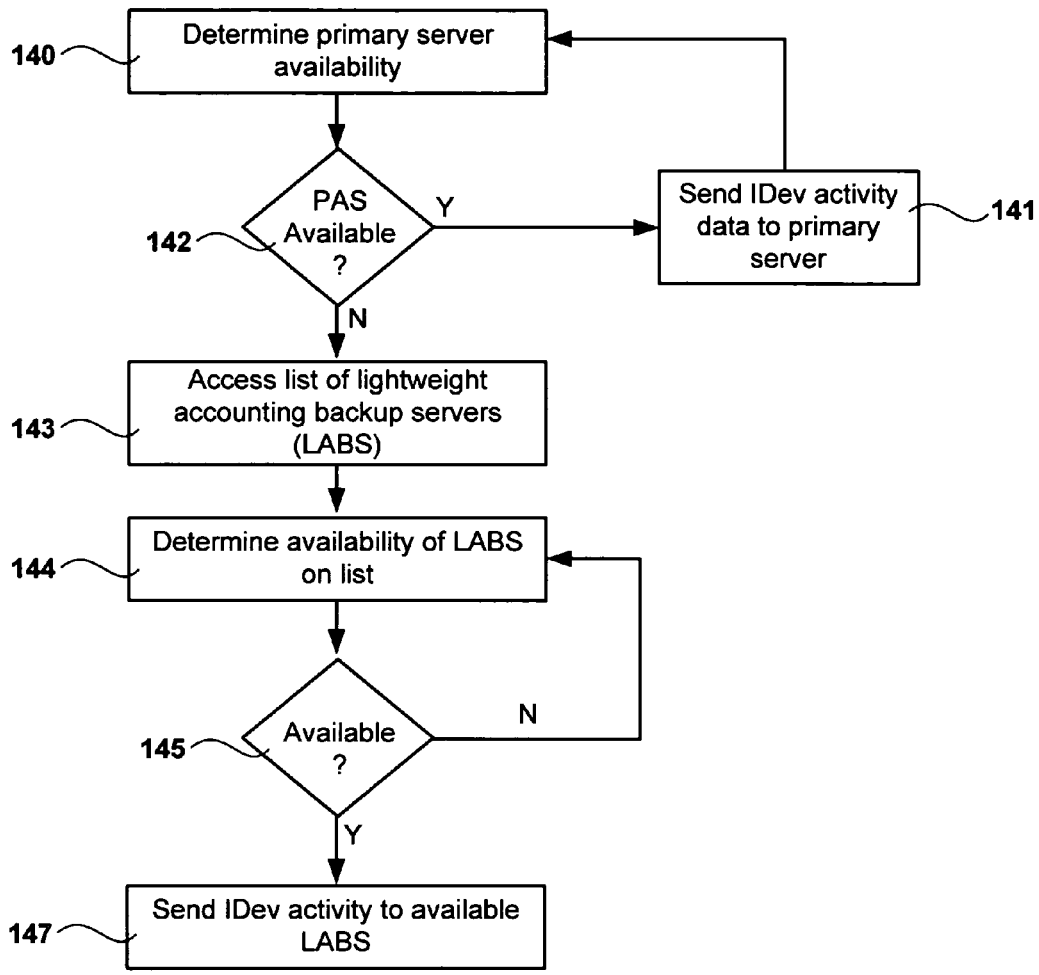
FIG. 14A is a chart showing the steps of a method of some embodiments comprising maintenance of IDev activity data in the event of a primary accounting server failure.

Some embodiments of the present invention may be described with reference to FIG. 14A. These embodiments comprise an accounting-controlled IDev that performs IDev functions for a user. The IDev may also provide access to remote applications to a user. Typically, a user will log on to the system by providing account data and user credentials and the IDev and/or associated local or remote applications will authenticate the user credentials and allow access to the system in relation to the user's account. When the user accesses IDev functions, local applications and/or remote applications, the IDev may monitor this activity and report the activity to an accounting server. This report may be made to a primary accounting server (PAS) or to a lightweight accounting back-up server (LABS) depending on the current status of the network and the servers.

When all servers, devices and network components are functioning properly (the PAS is available to the IDev), the IDev may determine 140 that a PAS is available and send 141 activity data to a primary accounting server (PAS). Alternatively, a message may be sent using an acknowledgement process to determine PAS availability. When a PAS is not available 142, the IDev may access 143 a list of LABS from the primary server and determine the availability 144 of a LABS on that list. When a LABS is determined to be available 145, the IDev may send 147 activity data to that LABS. The LABS may then keep a temporary IDev activity log (TIAL) for that IDev. If the LABS is not available 145, the IDev may progress down the list to another LABS and determine the availability 144 of each LABS until it finds an available LABS. The IDev may then send 147 its activity data to the available LABS. In some embodiments, this process may be followed for each activity message sent by the IDev. In other embodiments, once an available LABS is found, that LABS may be designated as the current accounting server (CAS) and all activity data will be sent to that server until a change in availability.

In some embodiments of the present invention, multiple LABS may be used by a single IDev or multiple IDevs. In some embodiments, regional LABS may be assigned to different regions of the area served by the PAS. When a PAS becomes unavailable, IDevs may report to regional LABS depending on their geographic location, account status, user credentials, IDev type or some other regional differentiator. Each region may have a series of LABS. In some embodiments, a regional LABS may have other regional LABS as back-up LABS listed in it's IDevs' lists.

Figure 14B:
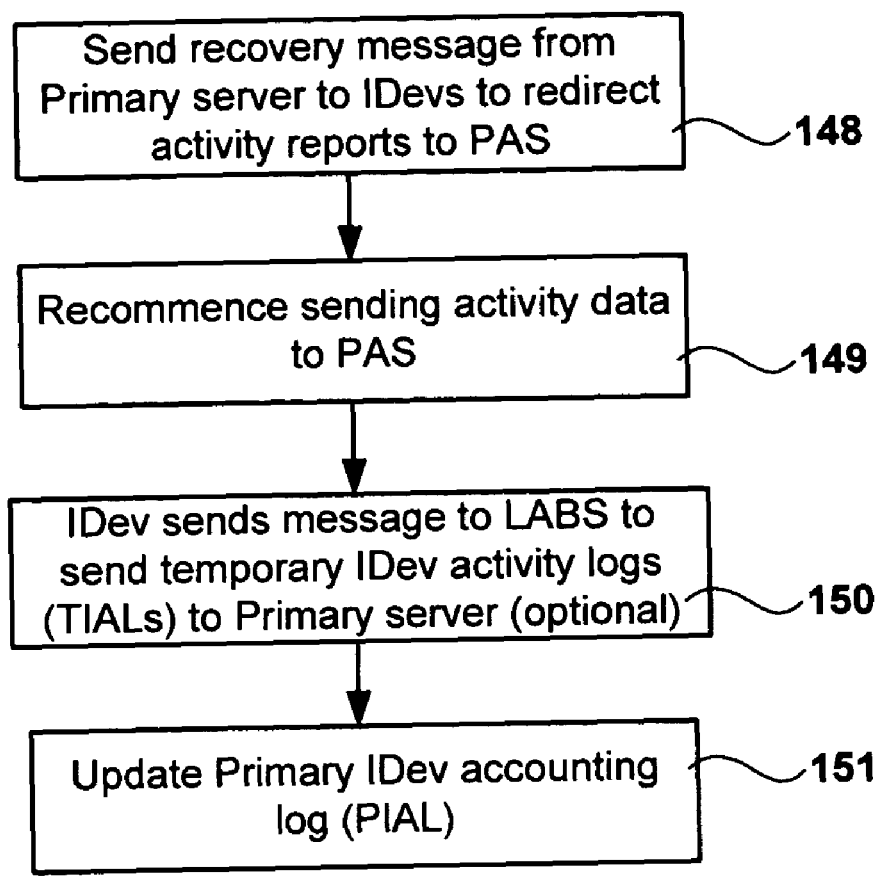
FIG. 14B is a chart showing the steps of a method of some embodiments comprising recovering temporary IDev activity data after a primary accounting server is put back into service.

Some embodiments of the present invention may be described with reference to FIG. 14B. The description of these embodiments illustrates a data recovery process that occurs when an unavailable PAS become available. In these embodiments, a PAS may send out a recovery message when it becomes available 148. When the IDevs receive the recovery message, they may re-commence 149 sending activity data to the PAS. In some embodiments, the LABS may also receive the recovery message and, in response, the LABS may send their temporary IDev activity logs (TIALs) to the PAS. In some embodiments, wherein the LABS does not receive the recovery message, the IDev may respond to the recovery message by sending 150 a message to the LABS instructing the LABS to send its TIAL to the PAS. Once the PAS has received TIAL data, the PAS may update 151 its primary IDev activity log (PIAL) with the temporary data logged while the PAS was unavailable.

Figure 15:
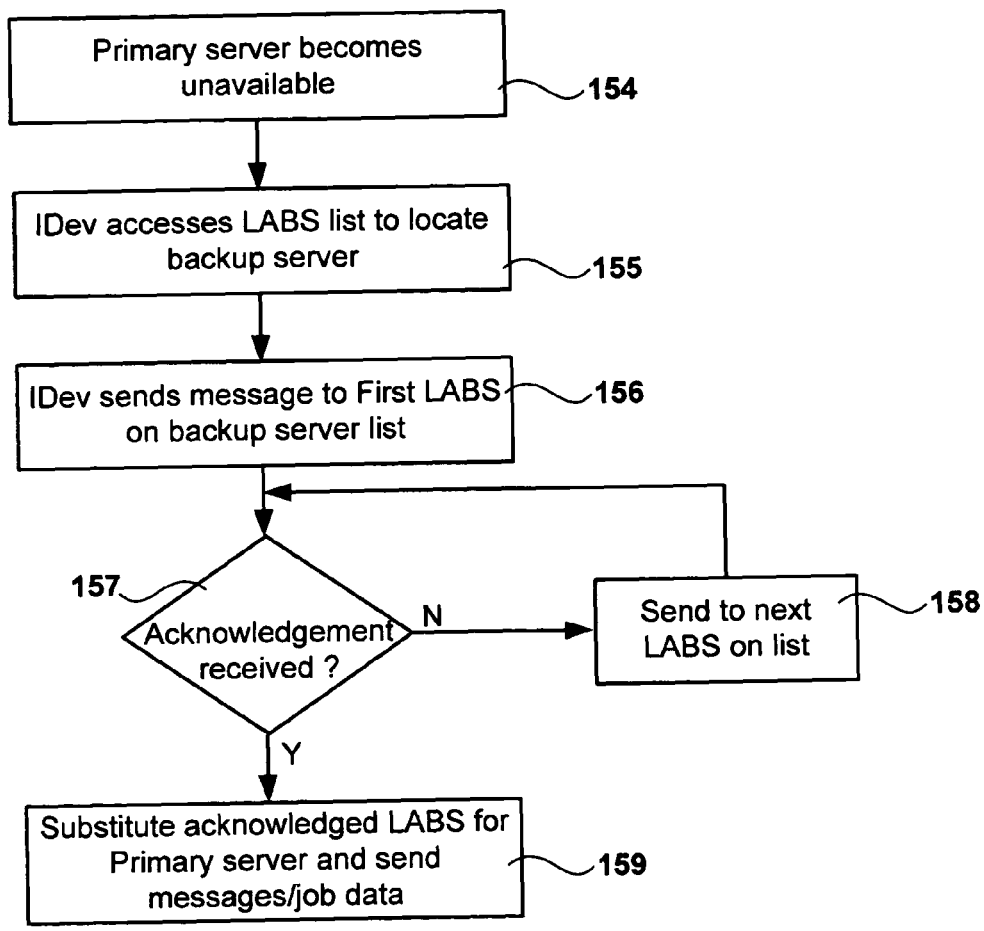
FIG. 15 is a chart showing the steps of a method of some embodiments comprising finding a LABS when a primary accounting server fails.

Some embodiments of the present invention may be described with reference to FIG. 15. These embodiments comprise an IDev that is capable of sending messages and activity data to a primary accounting server (PAS) and to a LABS. In some embodiments, the PAS and the LABS may also communicate directly. In these embodiments, when a PAS becomes unavailable, the IDev is no longer able to send activity data to the PAS. This may be detected by a message acknowledgement process, by pinging the PAS or by many other methods.

When the PAS become unavailable 154, the IDev may access 155 its LABS list to determine the address of an alternate LABS. The IDev may then determine the availability of a first LABS on the list. In some embodiments, this may be done by sending 156 a message to the first LABS on the list according to a send and acknowledge process. If an acknowledgement is received from the first LABS 157, the IDev may send 159 its activity data to the first LABS, which will then compile that data into a TIAL. If the first LABS does acknowledge 157 the message, the IDev may send a message to the next LABS on the list 158 and continue the process until a LABS acknowledges the process, receives the activity data and compiles a TIAL.

Figure 16:
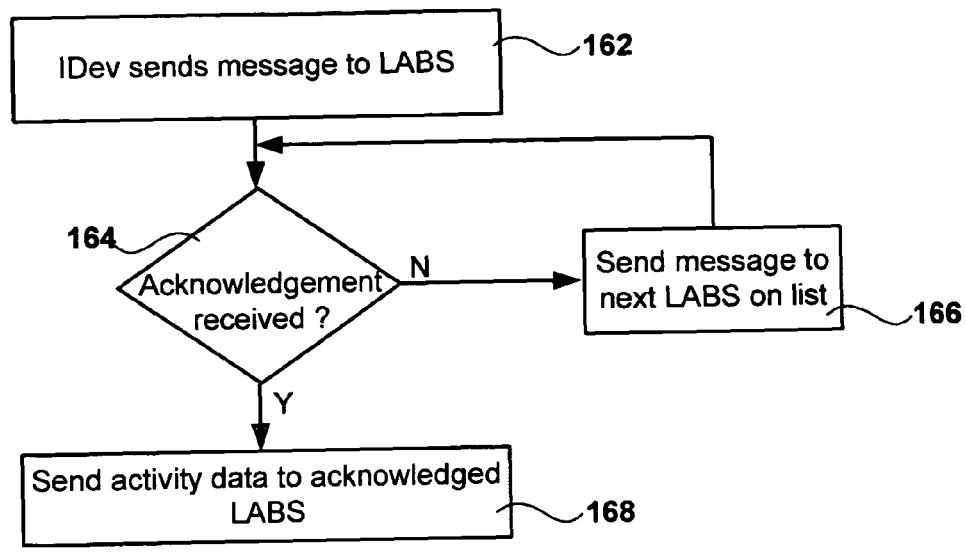
FIG. 16 is a chart showing the steps of a method of some embodiments comprising finding a new LABS when a current LABS fails.

Some embodiments of the present invention, illustrated in FIG. 16, comprise an IDev capable of communicating with a LABS. In these embodiments, these elements follow an exemplary process for maintaining activity data during a PAS failure followed by a LABS failure. In this exemplary process, an IDev sends activity data to a LABS, which compiles a TIAL. In these embodiments a send and acknowledge process is used, however, in alternative embodiments the availability of a LABS may be determine by other methods. An IDev may send 162 a message to an LABS in expectation of an acknowledgement (ACK). If an ACK is received 164, the IDev will continue sending 168 activity data to the LABS. If an ACK is not received 164, the IDev may access its LABS list and send a message 166 to the next LABS on the list in expectation of an ACK. This process will continue until the IDev's message receives an ACK at which point the IDev will send its activity data to the acknowledged LABS.

Figure 17:
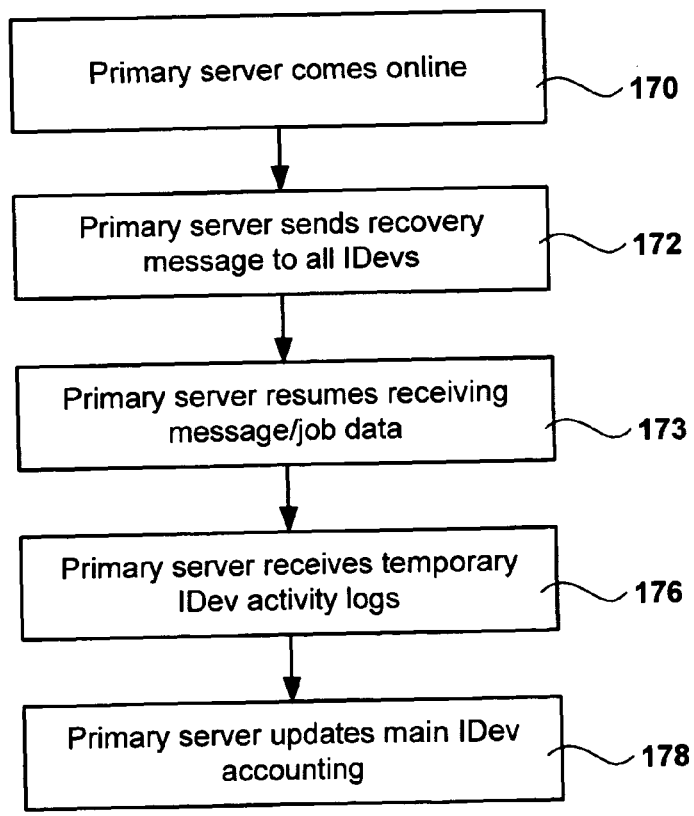
FIG. 17 is a chart showing the steps of a method of some embodiments comprising recovering temporary IDev activity data after a primary accounting server is put back into service.

Some embodiments of the present invention, illustrated in FIG. 17, comprise a method and/or system for recovering data to a primary accounting server (PAS) after a period of unavailability. In these embodiments, the PAS comes on-line 170 by connecting to the network with full functionality. The PAS then sends a recovery message 172 that may be received by any IDevs on the network as well as other devices. When an IDev receives the recovery message, the IDev may respond by recommencing the sending of its activity data 173 to the PAS. In some embodiments the IDev may respond to the recovery message by sending a message to the LABS instructing the LABS to send TIAL data to the PAS. The PAS will then receive 176 the TIAL data and update 178 its primary IDev activity log (PIAL) with the TIAL data.

Figure 18:
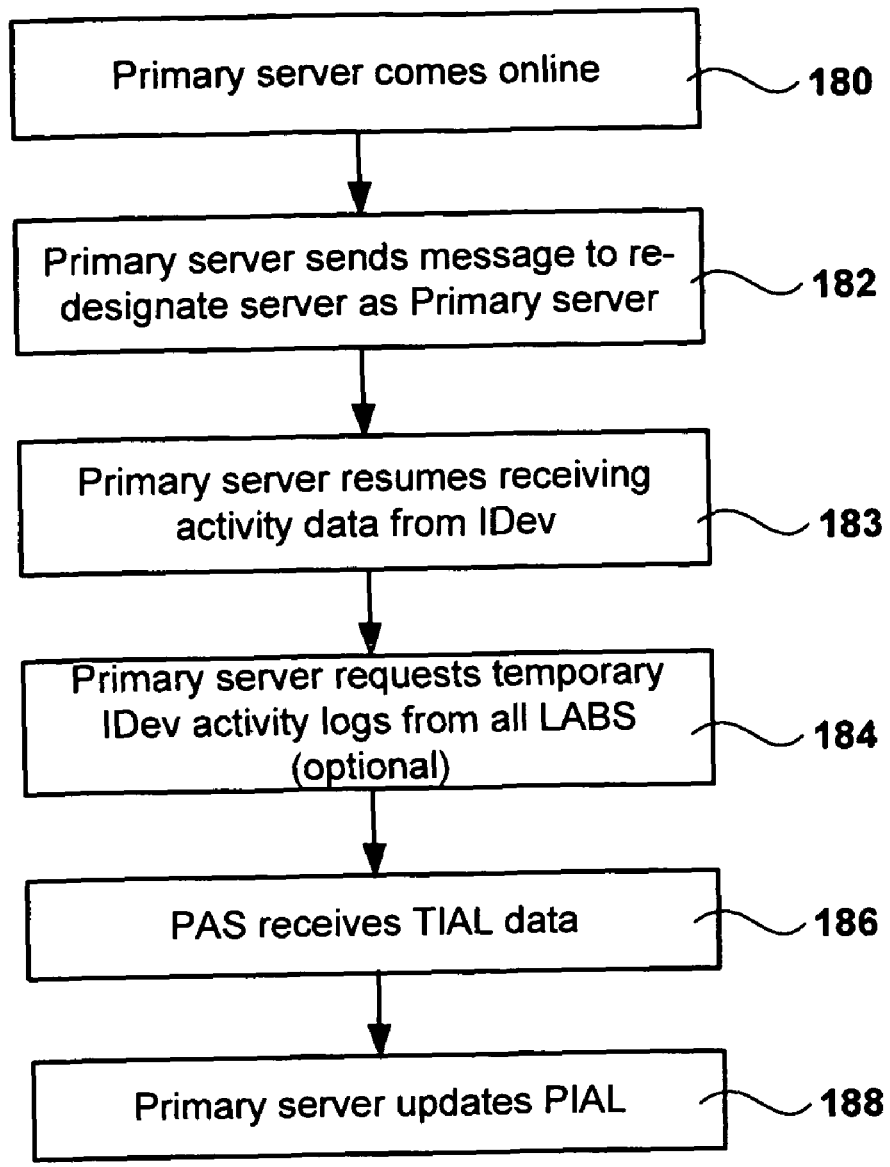
FIG. 18 is a chart showing the steps of a method of some embodiments comprising recovering temporary IDev activity data after a primary accounting server is put back into service.

Some embodiments of the present invention, illustrated in FIG. 18, comprise a method and/or system for recovering data to a primary accounting server (PAS) after a period of unavailability. In these embodiments, the PAS comes on-line 180 by connecting to the network with full functionality. The PAS then sends a recovery message 182 that may be received by any IDevs on the network as well as other devices, such as LABSs. When an IDev receives the recovery message, the IDev may respond by recommencing the sending of its activity data 183 to the PAS. In some embodiments a LABS may also respond to the recovery message by sending 184 any TIAL data the LABS has logged to the PAS. In some embodiments, the TIAL data may be sent in response to a specific request 184. The PAS may then receive 186 the TIAL data and update 188 its primary IDev activity log (PIAL) with the TIAL data.

The terms and expressions which have been employed in the forgoing specification are used therein as terms of description and not of limitation, and there is no intention in the use of such terms and expressions of excluding equivalence of the features shown and described or portions thereof, it being recognized that the scope of the invention is defined and limited only by the claims which follow.

We claim:

1. A method for maintaining imaging device (IDev) activity data in the event of a primary server failure, said method comprising:
   establishing a primary accounting server (PAS) for maintaining a primary IDev activity log (PIAL)), wherein said PAS is a computing device and said PIAL comprises a financial accounting record of jobs performed by users of said IDev with user accounts and said IDev is connected to said PAS with a first communication connection;
   establishing a lightweight accounting back-up server (LABS) on a device remote to said PAS for maintaining a temporary IDev activity log (TIAL) when said PAS is not available, wherein said LABS is a computing device and said TIAL comprises a financial accounting record of jobs performed by users of said IDev with said user accounts when said PAS is unavailable and said IDev is connected to said LABS with a second communication connection;
   listing said LABS on an LABS list accessible to a plurality of IDevs within a geographical region, wherein said LABS list consists of a listing of addresses for a plurality of network devices with LABS capability available only to said plurality of IDevs within said geographical region;
   sending IDev activity data from at least one of said plurality of IDevs within said geographical region to said PAS when said PAS is available;
   sending an availability request from said at least one of said IDevs within said geographical region to said LABS when said PAS is unavailable to said at least one of said plurality of IDevs within said geographical region;
   receiving an availability confirmation from said LABS at said at least one of said plurality of IDevs when said LABS is available and said PAS is unavailable;
   sending IDev activity data from said at least one of said plurality of IDevs to said LABS when said availability confirmation is received;
   incorporating said IDev activity data into a TIAL with said LABS;
   sending said TIAL from said LABS to said PAS after a period of unavailability of said PAS; and
   updating said PIAL with said TIAL after said period of unavailability such that said PIAL comprises transactions recorded on said IDev activity data when said PAS was unavailable.

2. A method as described in claim 1 wherein the availability of said PAS is determined by a send and acknowledge process.

3. A method as described in claim 1 wherein said period of inactivity of said PAS is terminated by a message from said PAS to said LABS wherein said TIAL data is requested.

4. A method as described in claim 1 wherein said period of inactivity of said PAS is terminated by a message from said PAS to said IDev wherein said TIAL data is requested and wherein said IDev requests said TIAL data from said LABS and forwards said TIAL data to said PAS.

5. A system for maintaining imaging device (IDev) accounting data, said system comprising:
   a plurality of networked client computing devices;
   at least one lightweight accounting back-up server application running on at least one of said networked computing devices and functioning as a lightweight accounting back-up server (LABS);
   a networked primary accounting server (PAS) networked with said client computing devices and said LABS; and
   a plurality of networked imaging devices (IDevs) in a specific geographical region;
   wherein said plurality of networked IDevs report their activity to said PAS when said PAS is available and said PAS maintains a primary IDev activity log (PIAL), comprising a financial accounting record of jobs performed by users of said IDevs with user accounts;
   a regional LABS list accessible to said plurality of networked IDevs within said specific geographical region, wherein said LABS list consists of a listing of addresses for a plurality of network devices with LABS capability available only to said plurality of networked IDevs within said specific geographical region and wherein said LABS is on said LABS list;
   wherein said plurality of IDevs in said specific geographical region determines the availability of said LABS, when said PAS is unavailable, by accessing said LABS list and sending an availability request to said LABS and receiving an availability confirmation from said LABS, and wherein said plurality of IDevs in said specific geographical region report their activity to said at least one LABS when said availability request is received;

wherein said at least one LABS maintains a temporary IDev activity log (TIAL), comprising a financial accounting record of jobs performed by users of said IDev with user accounts when said IDev reports to said LABS;

wherein said LABS reports to said PAS after a period of unavailability and sends said TIAL data to said PAS; and wherein said PAS updates said PIAL with said TIAL data such that said updated PIAL comprises a financial accounting record of jobs performed by users of said IDevs when said PAS was unavailable.

6. A system as described in claim 5 wherein said LABS reports to said at least one of said plurality of IDevs in said specific geographical region instead of said PAS after a period of unavailability, said LABS sends said TIAL data to said at least one of said plurality of IDevs in said specific geographical region and said at least one of said plurality of IDevs in said specific geographical region forwards said TIAL data to said PAS.

7. A system as described in claim 5 wherein said LABS list lists said LABSs in a hierarchical order in which LABSs are prioritized.

8. A system as described in claim 5 wherein said at least one LABS comprises a plurality of LABS accessible in a sequential order thereby forming a multiple redundant back-up server system.

9. A system as described in claim 5 wherein PAS sends an update message to said plurality of IDevs in said specific geographical region after a period of unavailability and, in response to said update message, said plurality of IDevs in said specific geographical region renews sending a records of their activity to said PAS, request said TIAL data from said LABS and send said TIAL data to said PAS.

10. A system as described in claim 5 wherein said PAS sends an update message to said LABS after a period of unavailability and, in response to said update message, said LABS sends said TIAL data to said PAS.

11. A system as described in claim 5 further comprising an accounting application for reporting said PIAL data to a user.

12. A system as described in claim 5 wherein a user at said networked client computing devices may use said IDev and said system will maintain a log of said user's activity.

* * * * *